(12) United States Patent
Chafe et al.

(10) Patent No.: US 9,888,884 B2
(45) Date of Patent: Feb. 13, 2018

(54) METHOD OF SONIFYING SIGNALS OBTAINED FROM A LIVING SUBJECT

(71) Applicant: The Board of Trustees of the Leland Stanford Junior University, Palo Alto, CA (US)

(72) Inventors: Christopher D. Chafe, Palo Alto, CA (US); Josef Parvizi, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 399 days.

(21) Appl. No.: 14/557,240

(22) Filed: Dec. 1, 2014

(65) Prior Publication Data

US 2015/0150520 A1 Jun. 4, 2015

Related U.S. Application Data

(60) Provisional application No. 61/910,939, filed on Dec. 2, 2013, provisional application No. 61/914,567, filed on Dec. 11, 2013.

(51) Int. Cl.
*A61B 5/046* (2006.01)
*A61B 5/0452* (2006.01)
(Continued)

(52) U.S. Cl.
CPC ............ *A61B 5/7415* (2013.01); *A61B 5/046* (2013.01); *A61B 5/0452* (2013.01); *A61B 5/0482* (2013.01)

(58) Field of Classification Search
CPC ..... A61B 5/0452; A61B 5/046; A61B 5/0482; A61B 5/7415

(Continued)

(56) References Cited

U.S. PATENT DOCUMENTS

| 4,018,121 A | 4/1977 | Chowning |
| 4,883,067 A * | 11/1989 | Knispel ............... A61B 5/0482 |
| | | 600/28 |

(Continued)

OTHER PUBLICATIONS

Baier et al., "The Sonification of Rhythms in Human Electroencephalogram," Proceedings of ICAD 04-Tenth Meeting of the International Conference on Auditory Display, Sydney, Australia, Jul. 6-9, 2004, 5 pgs.

(Continued)

*Primary Examiner* — Navin Natnithithadha
(74) *Attorney, Agent, or Firm* — Lumen Patent Firm

(57) ABSTRACT

A digital processor system obtains at least one time-domain signal representing brain activity and at least one time-domain signal representing heart activity, each having a time-varying signal value. The system produces representations of a plurality of acoustic signals, each of which corresponds to a respective time-domain signal and is produced by concurrently generating a plurality of acoustic parameters, including a plurality of time-varying acoustic parameters. One or more of the plurality of time-varying acoustic parameters is modulated in accordance with at least the signal value of the respective time-domain signal. Each representation of an acoustic signal of the plurality of acoustic signals is further produced by combining the concurrently generated plurality of acoustic parameters to produce the representation of the acoustic signal corresponding to the respective time-domain signal. The system combines the representations of each of the plurality of acoustic signals to produce a combined acoustic signal.

24 Claims, 15 Drawing Sheets

(51) Int. Cl.
*A61B 5/0482* (2006.01)
*A61B 5/00* (2006.01)

(58) Field of Classification Search
USPC ........ 600/481, 483, 508, 509, 513, 544, 545
See application file for complete search history.

(56) References Cited

U.S. PATENT DOCUMENTS

| | | | |
|---|---|---|---|
| 5,730,140 A | 3/1998 | Fitch | |
| 7,881,778 B2 | 2/2011 | Rantala | |
| 8,620,643 B1 | 12/2013 | Ludwig | |
| 8,644,915 B2 | 2/2014 | Chou | |
| 8,885,464 B2 | 11/2014 | Micu et al. | |
| 9,330,680 B2* | 5/2016 | Kassam | G10L 25/48 |
| 2007/0218084 A1 | 9/2007 | Caleo et al. | |
| 2008/0269633 A1 | 10/2008 | Watson | |
| 2009/0316925 A1* | 12/2009 | Eisenfeld | A61B 7/008 381/67 |
| 2012/0197092 A1 | 8/2012 | Lou et al. | |
| 2013/0324878 A1* | 12/2013 | Chafe | A61B 5/7415 600/544 |
| 2014/0074479 A1* | 3/2014 | Kassam | G10H 1/0025 704/270 |

OTHER PUBLICATIONS

Hermann et al., "Vocal Sonification of Pathologic EEG Features," Proceedings of the 12th International Conference on Auditory Display, London, UK, Jun. 20-23, 2006, 6 pgs.

Plessey Semiconductors Ltd., Epic . . . ECG at your fingertips, EPIC Healthcare—Plessey Semiconductors, printed Nov. 21, 2013 from www.plesseysemiconductors.com/epic-healthcare-plessey-semiconductors.php, 6 pgs.

Plessey Semiconductors Ltd., EPIC Healthcare—Plessey Semiconductors, printed Nov. 21, 2013 from http://www.plesseysemiconductors.com/epic-healthcare-plessey-semiconductors.php, 4 pgs.

Plessey Semiconductors Ltd., Application Note #291474, ECG sensor in a SmartPhone, Dec. 2, 2011, 2 pgs.

Plessey Semiconductors Ltd., Application Note #291566, Non-contact ECG measurement using EPIC, Mar. 22, 2012, 5 pgs.

Polar USA, Polar Wearlink® + Transmitter with Bluetooth®, printed Nov. 21, 2013 from http://www.polar.com/us-en/products/accessories/Polar WearLink transmitter with Blu . . . , 2 pgs.

Terasawa et al., "Sonifying ECOG Seizure Data with Overtone Mapping: A Strategy for Creating Auditory Gestalt from Correlated Multichannel Data," The 18th International Conference on Auditory Display (ICAD-2012), Jun. 18-22, 2012, Atlanta, USA, 6 pgs.

WebMD, What is an Electrocardiogram (EKG or ECG) Test?, Heart Disease Health Center, Electrocardiogram, printed Nov. 21, 2013 from http://www.webmd.com/heart-disease/electrocardiogram, 5 pgs.

Wikipedia, the free encyclopedia, Holter monitor, Jan. 14, 2015, printed Feb. 17, 2016 from https://en.wikipedia.org/wiki/Holter_monitor, 5 pgs.

Baier et al., "Event-based sonificaton of EEG rhythms in real time," Clinical Neurophysiology, Jun. 2007;118(6):1377-1386, Epub Mar. 29, 2007, 10 pgs.

Baier et al., "Sonified Epileptic Rhythms," Proceedings of the 12th International Conference on Auditory Display, London, UK, Jun. 20-23, 2006, 4 pgs.

Chafe, Office Action, U.S. Appl. No. 13/905,377, filed Apr. 12, 2016, 18 pgs.

Kleiman-Weiner et al., "The sound of One Arm Swinging: A Model for Multidimensional Auditory Display of Physical Motion," Proceedings of the 12th International Conference on Auditory Display, London, UK, Jun. 20-23, 2006, 3 pgs.

Vialatte et al., "Sparse Bump Sonification: A New Tool for Multi-channel EEG Diagnosis of Mental Disorders; Application to the Detection of the Early of Alzheimer's Disease," ICONIP 2006, Part III, LNCS 4234, pp. 92-101, 2006, 10 pgs.

\* cited by examiner

600

602 — Obtain two or more time-domain signals, including at least one time-domain signal representing brain activity and at least one time-domain signal representing heart activity, each of the one or more time-domain signals having a time-varying signal value

604 — The at least one time-domain signal representing brain activity is obtained by conditioning a sensor time-domain signal obtained from a sensor embedded in a particular location of a brain

606 — The at least one time-domain signal representing brain activity is obtained by conditioning a first sensor time-domain signal obtained from a first dry-contact sensor.

The at least one time-domain signal representing heart activity is obtained by conditioning a second sensor time-domain signal obtained from a second dry-contact sensor.

608 — The conditioning of a respective sensor time-domain signal includes upsampling the respective sensor time-domain signal to produce an intermediate signal and low pass filtering the intermediate signal to produce a respective time-domain signal

610 — Produce representations of a plurality of acoustic signals.

Each representation of an acoustic signal of the plurality of acoustic signals corresponds to a respective time-domain signal of the two or more time-domain signals.

612 — For each respective representation of an acoustic signal, concurrently generate a plurality of acoustic parameters, including a plurality of time-varying acoustic parameters.

One or more of the plurality of time-varying acoustic parameters is modulated in accordance with at least the signal value of the respective time-domain signal.

METHOD OF SONIFYING SIGNALS OBTAINED FROM A LIVING SUBJECT

RELATED APPLICATIONS

This application claims priority to U.S. Provisional Patent Application No. 61/910,939, filed Dec. 2, 2013, and U.S. Provisional Patent Application No. 61/914,567, filed Dec. 11, 2013, both of which are hereby incorporated by reference in their entireties.

This application is related to U.S. patent application Ser. No. 13/905,377 filed May 30, 2013, and U.S. Provisional Patent Application No. 61/653,370, filed May 30, 2012, which are hereby incorporated by reference in their entireties.

TECHNICAL FIELD

The disclosed embodiments relate generally to the field of detecting signals from a living subject (e.g., electrical signals indicative of brain activity and/or heart activity), and in particular, to a system and method of sonifying signals from a living subject.

BACKGROUND

The ability to measure signals from a living subject (e.g., relating to the living subject's bodily functions) is beneficial for medical and diagnostic applications as well as for scientific research. For example, from a diagnostic point of view, measuring brain signals helps to ascertain brain activity related to abnormal brain function, to monitor spatial and/or temporal progression of brain disease, to aid surgical or nonsurgical intervention by localizing disease-sites in the brain, and to monitor brain activity of a healthy subject or a subject of unknown health status when the subject experiences a variety of stimuli and lack of stimuli. Likewise, measuring heart signals helps to diagnose both chronic and acute cardiac arrhythmias, other deficits in cardiac function, and potentially to monitor heart activity of a healthy subject or a subject of unknown health status when the subject experiences a variety of stimuli and lack of stimuli. From a scientific perspective, the ability to measure and study signals from a living subject (e.g., a human subject) facilitates scientific research aimed at understanding the structure and function of the human body.

SUMMARY

Traditional methods of measuring and analyzing signals from a living subject have not focused on sonification (e.g., aural presentation) of the signals. Moreover, applications beyond diagnostics and scientific research (e.g., applications in entertainment, therapy, etc.) have been largely neglected.

Accordingly, some embodiments provide a system and method for sonifying electrical signals obtained from a living subject. The method includes obtaining two or more time-domain signals, including at least one time-domain signal representing brain activity and at least one time-domain signal representing heart activity. Each of the one or more time-domain signals has a time-varying signal value. The method further includes producing representations of a plurality of acoustic signals. Each representation of an acoustic signal of the plurality of acoustic signals corresponds to a respective time-domain signal of the two or more time-domain signals. Moreover, each representation of an acoustic signal of the plurality of acoustic signals is produced by concurrently generating a plurality of acoustic parameters, including a plurality of time-varying acoustic parameters. One or more of the plurality of time-varying acoustic parameters is modulated in accordance with at least the signal value of the respective time-domain signal. Each representation of an acoustic signal of the plurality of acoustic signals is further produced by combining the concurrently generated plurality of acoustic parameters to produce the representation of the acoustic signal corresponding to the respective time-domain signal. The method further includes combining the representations of each of the plurality of acoustic signals to produce a combined acoustic signal.

In another aspect, a method of sonifying signals obtained from a living subject is provided. The method includes obtaining a first time-domain electrical signal representing a first bodily function of the subject and a second time-domain electrical signal representing a second bodily function of the subject. The second bodily function is anatomically distinct from the first bodily function. The method further includes producing representations of a plurality of acoustic signals. Each representation of an acoustic signal of the plurality of acoustic signals corresponds to a time-domain signal. Moreover, each representation of an acoustic signal of the plurality of acoustic signals is produced by concurrently generating a plurality of acoustic parameters, including a plurality of time-varying acoustic parameters. One or more of the plurality of time-varying acoustic parameters is modulated in accordance with at least the signal value of the time-domain signal. Each representation of an acoustic signal of the plurality of acoustic signals is further produced by combining the concurrently generated plurality of acoustic parameters to produce the representation of the acoustic signal corresponding to the respective time-domain signal. The method further includes combining the representations of each of the plurality of acoustic signals to produce a combined acoustic signal.

In accordance with some embodiments, a computer system (e.g., a client system or server system) includes one or more processors, memory, and one or more programs; the one or more programs are stored in memory and configured to be executed by the one or more processors and the one or more programs include instructions for performing the operations of the method described above. In accordance with some embodiments, a non-transitory computer readable storage medium has stored therein instructions which when executed by one or more processors, cause a computer system (e.g., a client system or server system) to perform the operations of the methods described above.

BRIEF DESCRIPTION OF THE DRAWINGS

FIGS. 6A-6F include a flow chart illustrating a method for sonifying signals obtained from a living subject, in accordance with some embodiments.

Like reference numerals refer to corresponding parts throughout the drawings.

DESCRIPTION OF EMBODIMENTS

Figure 1:
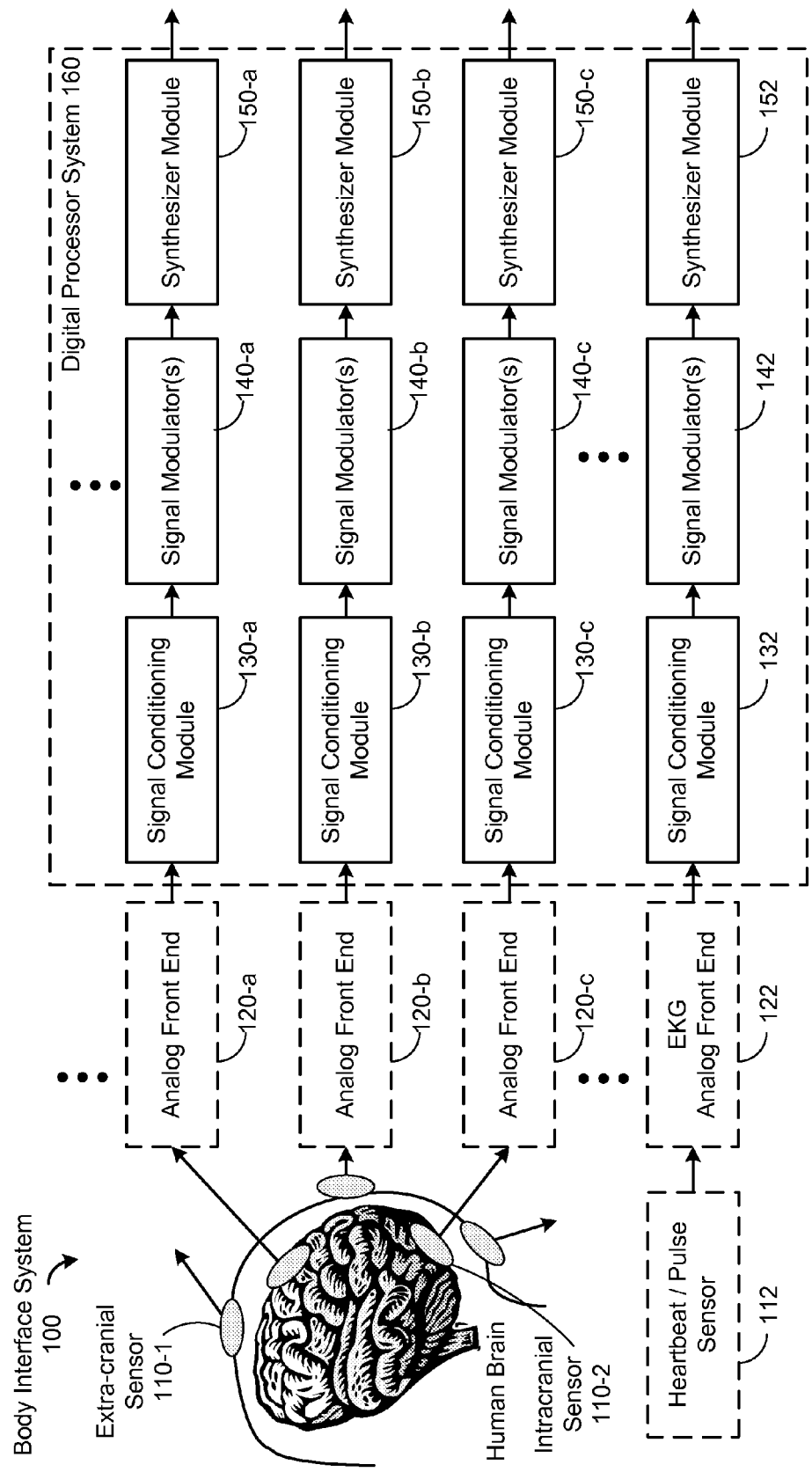
FIG. 1 illustrates a body interface system for acquiring and processing signals from a living subject, in accordance with some embodiments.

Traditional approaches to measuring signals from a living subject (e.g., location-specific brain signals, or electrocardiography (ECG) signals corresponding to heart activity) typically involve recording and visually displaying electrical signals acquired from the brain or other organs. Moreover, these approaches are typically used for diagnostic or scientific purposes. When represented in visual or graphical form, subtle features and attributes—and subtle changes in features and attributes—of the electrical signals may not be easily discernible. However, when sonified or converted to auditory form, these subtle features and attributes can become more apparent. Furthermore, sonification methodologies that transform the signals acquired from the living subject into vocal patterns and vocal parameters—and changes in vocal patterns and vocal parameters—that resemble a human voice make it easier to discern, upon auditory inspection, subtleties in the underlying electrical signals that correspond to bodily function.

Additionally, traditional approaches to measuring signals from a living subject have not focused on applications beyond diagnostics and scientific research. To that end, a method of sonifying signals obtained from a living subject is provided. In particular, in some embodiments, the method transforms signals acquired from the living subject into vocal patterns and vocal parameters that can be used for applications in entertainment as well as user interfaces for electronic devices.

The method includes obtaining a first time-domain electrical signal representing a first bodily function of the subject and a second time-domain electrical signal representing a second bodily function of the subject, the second bodily function being anatomically distinct from the first bodily function (e.g., the first bodily function and the second bodily function correspond to distinct bodily organs, such as the brain, heart, or a muscle, or organ systems, such as the circulatory system, muscular system, or nervous system). In some embodiments, the first time-domain electrical signal and/or the second time-domain electrical signal measure a metric associated with a non-electrical bodily function that is converted to an electrical signal by a measurement apparatus. For example, in some embodiments, the first time-domain electrical signal and/or the second time-domain electrical signal is one of a pulse oximetry signal, a capnography signal, a photoplethysmography signal, or the like. Alternatively, the first time-domain electrical signal and/or the second time-domain electrical signal measure an electrical activity of the body (e.g., using electrodes). For example, in some embodiments, the first time-domain electrical signal and/or the second time-domain electrical signal measure an electrocardiography (ECG) signal, an electroencephalography (EEG) signal, an electromyography (EMG) signal, an electronystagmography (ENG) signal, or the like.

The method includes producing representations of a plurality of acoustic signals. Each representation of an acoustic signal of the plurality of acoustic signals corresponds to a time-domain signal and is produced by concurrently generating a plurality of acoustic parameters, including a plurality of time-varying acoustic parameters. One or more of the plurality of time-varying acoustic parameters is modulated in accordance with at least the signal value of the time-domain signal. Each representation of an acoustic signal of the plurality of acoustic signals is further produced by combining the concurrently generated plurality of acoustic parameters to produce the representation of the acoustic signal corresponding to the respective time-domain signal.

In some implementations, the method further includes combining the representations of each of the plurality of acoustic signals to produce a combined acoustic signal. In some other implementations, two or more of the representations of the acoustic signals are recorded on separate tracks, or directed to distinct speakers, for concurrent production as acoustic signals. As a result, a combined acoustic signal, corresponding to representations of the plurality of acoustic signals, is generated (e.g., generated "in the air") by concurrent production of two or more individual acoustic signals within a physical space or in a manner that enables the concurrently produced acoustic signals to be heard concurrently by a human listener.

For example, some embodiments described below combine sonified signals from the living subject's heart with signals from the living subject's brain to produce a combined acoustic signal. The combined acoustic signal, in audible form, manifests one or more audibly discernible variations of the living subject's response to an external stimulus (e.g., visual, and/or aural). For example, in some embodiments, the external stimulus includes music (to which the living subject is listening), a video game (e.g., a video game played by the living subject or watched by the living subject), a physical game (e.g., a video game played by the living subject or watched by the living subject), and/or exercise, and the combined acoustic signal is provided to the subject as a custom soundtrack. In some embodiments, the combined acoustic signal is aurally provided to the living subject in real-time as biofeedback, for example as a neurofeedback for neurotherapy (e.g., the combined acoustic signal comprises a hemoencephalography (HEG) feedback signal). In some embodiments, the neurotherapy comprises a therapy for at least one of: migraines, autism, attention deficit hyperactivity disorder (ADHD), and/or cognitive performance.

In some implementations, the combined acoustic signal produced by performance of any of the sonification methods described herein is provided to a living person (sometimes called the second person for ease of reference) other than the living subject (sometimes called the first person for ease of reference) whose brain activity, heart activity, and/or other bodily functions are monitored and sonified using any of the sonification methods described herein. For example, the second person listens to the combined acoustic signal of the first person while the first person performs an activity, such as listening to music, conversing with the second person, playing or watching a video game, playing or watching a physical game, exercising, reading a document, engaging in a particular mental activity such as solving a problem or puzzle, counting backwards, detecting a pattern in information presented visually and/or audibly, etc. In some implementations, the sonification method described herein is performed, independently, on first and second living subjects, producing first and second combined acoustic signals corresponding to the first and second living subjects, respectively, and providing the first combined acoustic signal to the second living subject and providing the second combined acoustic signal to the first living subject. In some implementations, any of the aforementioned methods are performed while monitoring only brain activity of the living subject (or both living subjects), or while monitoring only one bodily function (e.g., monitoring a heart activity signal or any other bodily function signals) of the living subject (or both living subjects).

In some embodiments, the sonification methodologies described herein are encoded within instructions that comprise an application (e.g., an "app") on a portable multi-function device (e.g., an exercise app or a gaming app). In some embodiments, the application interfaces with one or more dry-sensors (e.g., conductive sensors that are mechanically placed against a living subject's body rather implanted within the living subject's body or held in place with a sticky conductive gel).

Reference will now be made in detail to various embodiments, examples of which are illustrated in the accompanying drawings. In the following detailed description, numerous specific details are set forth in order to provide a thorough understanding of the invention and the described embodiments. However, the invention is optionally practiced without these specific details. In other instances, well-known methods, procedures, components, and circuits have not been described in detail so as not to unnecessarily obscure aspects of the embodiments.

It will be understood that, although the terms "first," "second," etc. are optionally used herein to describe various elements, these elements should not be limited by these terms. These terms are only used to distinguish one element from another. For example, a first sensor could be termed a second sensor, and, similarly, a second sensor could be termed a first sensor, without changing the meaning of the description, so long as all occurrences of the "first sensor" are renamed consistently and all occurrences of the second sensor are renamed consistently. The first sensor and the second sensor are both sensors, but they are not the same sensor.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is optionally construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" is optionally construed to mean "upon determining" or "in response to determining" or "in accordance with a determination" or "upon detecting" or "in response to detecting" that the stated condition precedent is true, depending on the context.

Figure 2A:
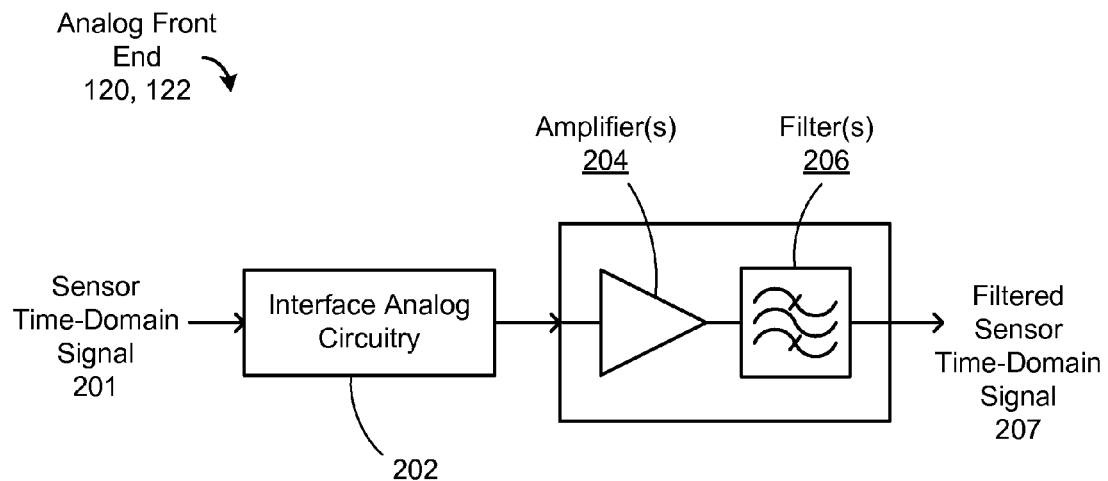
FIG. 2A is a block diagram illustrating an analog front end used for pre-processing electrical signals obtained from a living subject, in accordance with some embodiments.
Figure 2B:
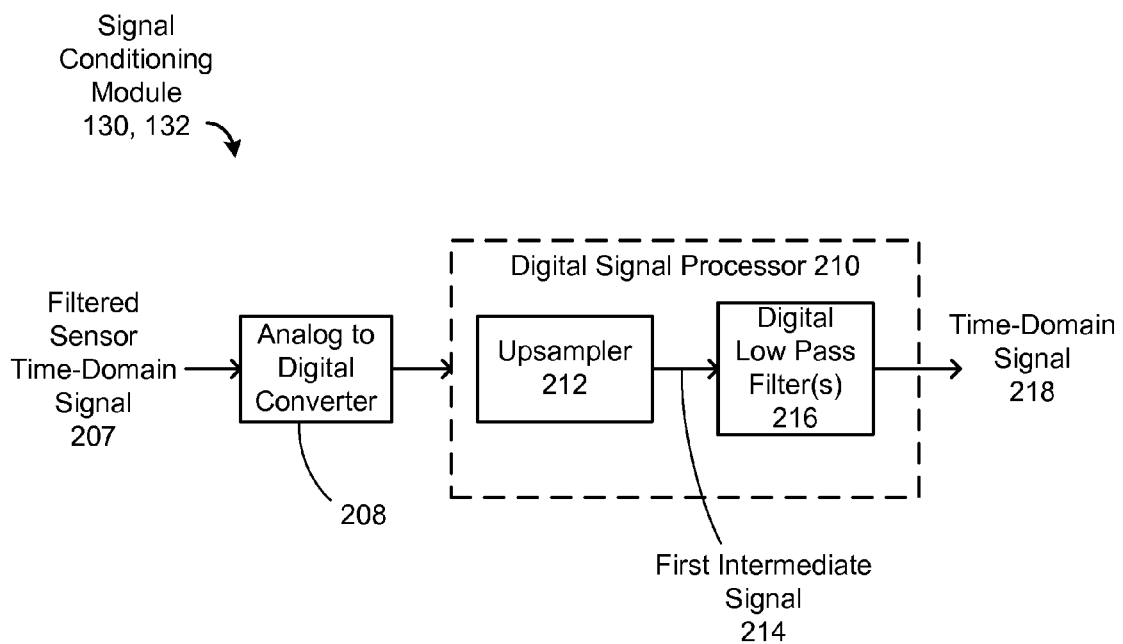
FIG. 2B is a block diagram illustrating a signal conditioning module used for processing electrical signals obtained from a living subject, in accordance with some embodiments.
Figure 2C:
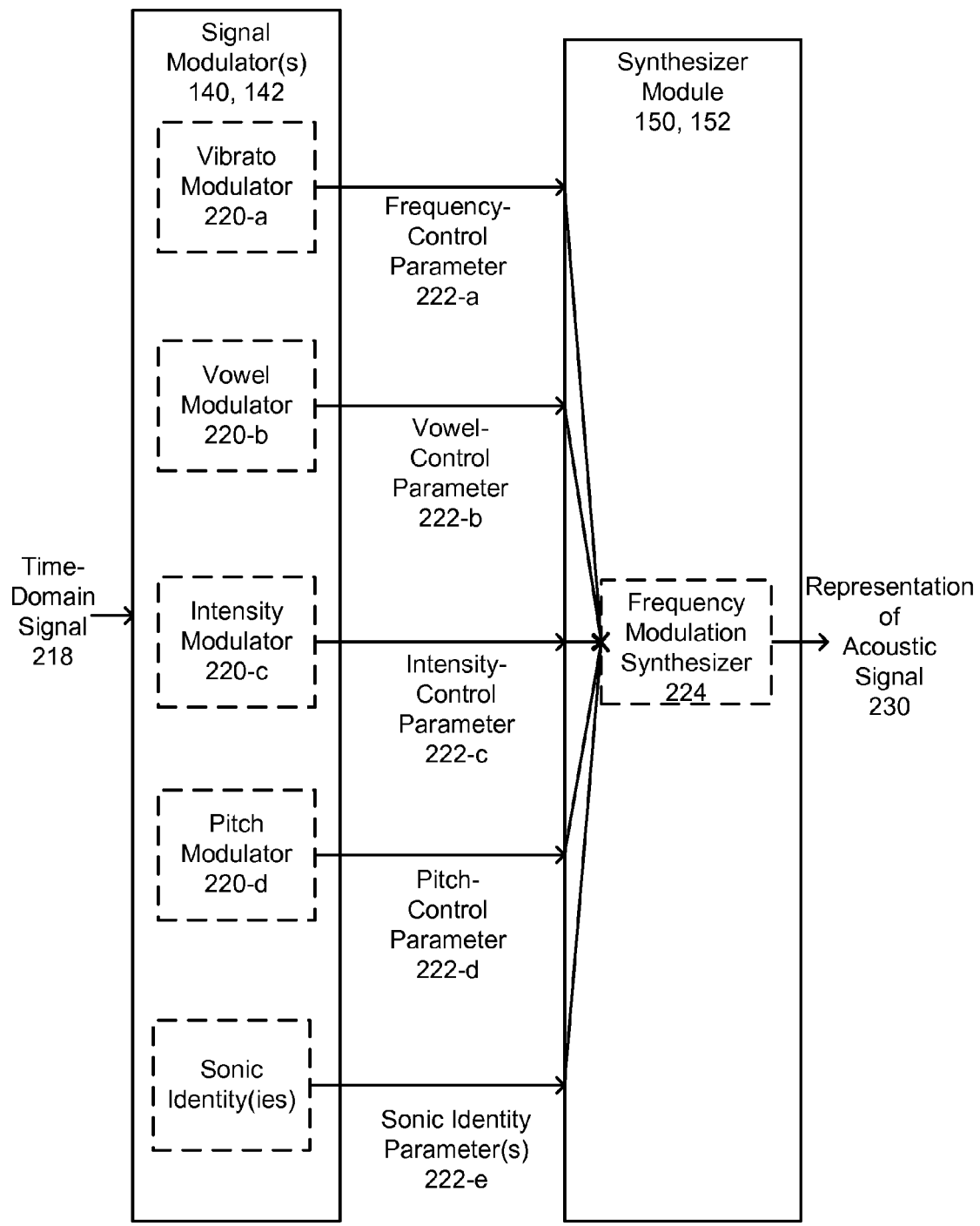
FIG. 2C is a block diagram illustrating signal modulators and a synthesizer module used for processing electrical time-domain signals obtained from a living subject to produce a representation of an acoustic signal, in accordance with some embodiments.
Figure 2D:
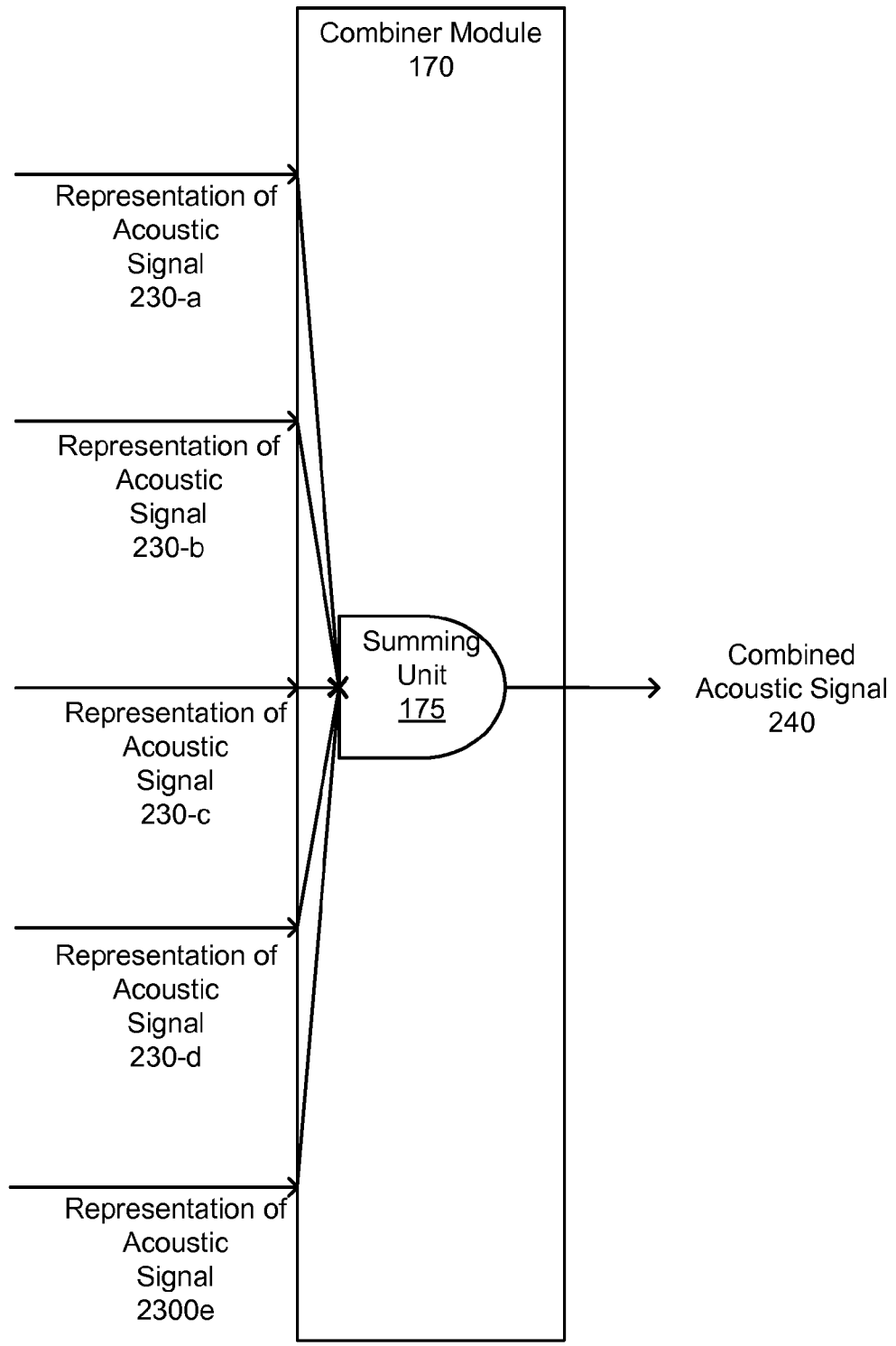
FIG. 2D is a block diagram of a combiner module used for combining a plurality of representations of acoustic signals, in accordance with some embodiments.
Figure 3:
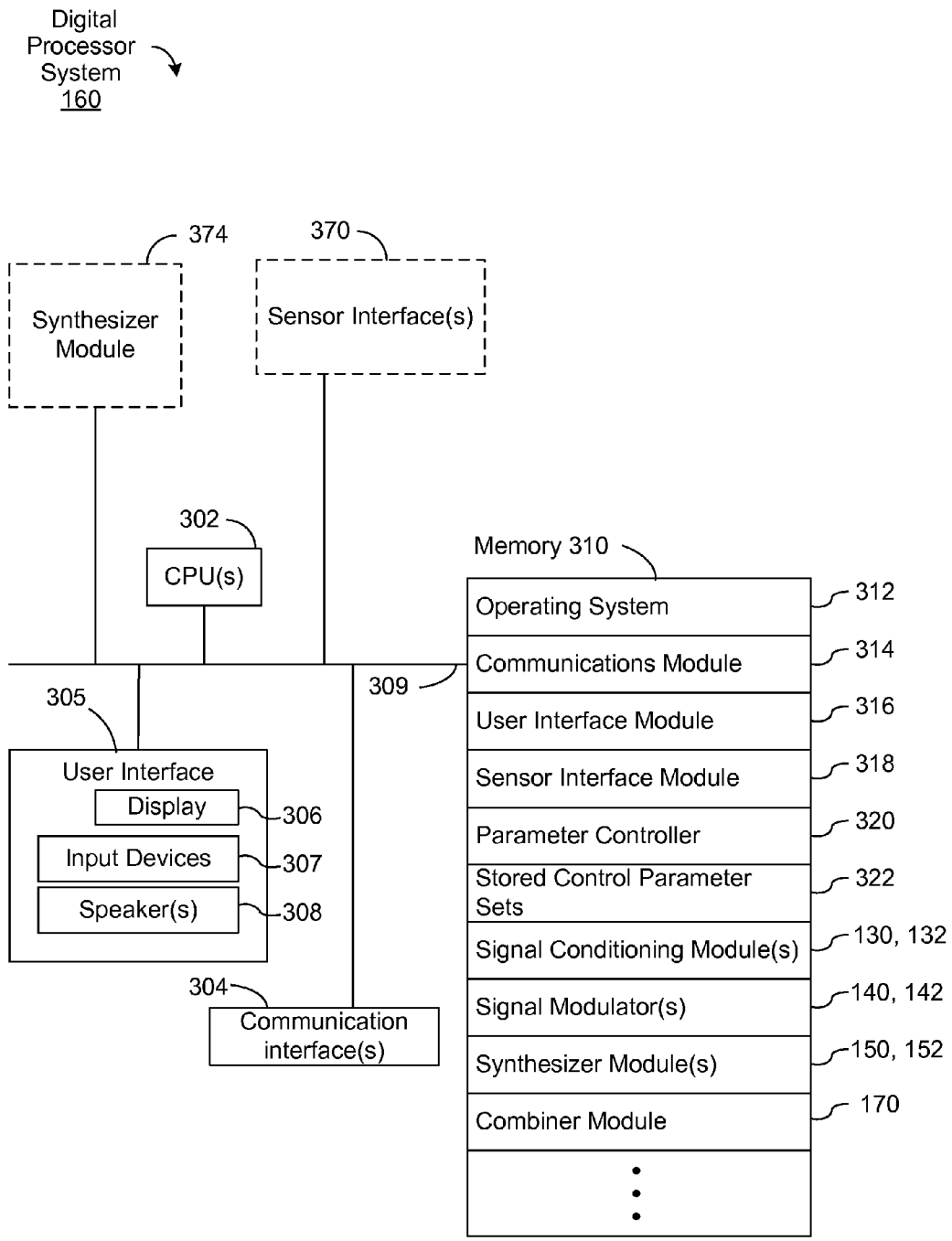
FIG. 3 is a block diagram illustrating a digital processor used for processing signals representing bodily functions, in accordance with some embodiments.

For ease of explanation, FIGS. 1-3 are described below with reference to sonification of signals representing brain activity (e.g., electroencephalography (EEG) signals) and/or heart activity (e.g., electrocardiography (ECG) signals) of a living subject. However, one of skill in the art will recognize that signals representing other bodily functions (e.g., an electromyography (EMG) signal, or an electronystagmography (ENG) signal, a pulse oximetry signal, a capnography signal, and/or a photoplethysmography signal) may be substituted, or used in addition to (e.g., in conjunction with), one or more signals representing brain activity and/or heart activity.

FIG. 1 illustrates body interface system 100 for sensing, acquiring and processing one or more signals (typically two or more signals) obtained from a living subject (e.g., obtained from a human's brain and/or heart) to produce a representation of an acoustic signal corresponding to the one or more (or two or more) signals (e.g., representing brain and/or heart activity). In some circumstances, body interface system 100 is deployed in a clinical setting (e.g., during or before surgical interventions and/or during diagnosis and/or treatment of conditions, such as epileptic seizures) for aural (e.g., auditory) measurement or monitoring of brain activity. Alternatively, or in addition, body interface system 100 is deployed as part of a user interface for a portable electronic device (e.g., a smart-phone, tablet, or the like) for entertainment, biofeedback, monitoring, therapeutic or other purposes.

In some embodiments, as shown in FIG. 1, body interface system 100 includes one or more sensor(s) 110, optionally includes one or more analog front end(s) 120 (e.g., one or more analog front end modules), one or more electrocardiography (ECG) analog front end(s) 122, and a digital processor system 160 (herein often called digital processor 160 for ease of reference). In some other embodiments, analog front end 122 is an analog front end for a sensor other than a heartbeat or pulse sensor.

In some embodiments, sensor(s) 110 are provided to interface with a living subject's brain to obtain (e.g., sense and/or acquire) sensor time-domain signals (e.g., sensor time-domain signal 201, FIG. 2A) corresponding to brain electrical activity. For example, signals (e.g., sensor time-domain signal 201, FIG. 2A) corresponding to brain electrical activity are obtained from a human brain and correspond to electrical signals obtained from a single neuron or from a plurality of neurons. In some embodiments, sensor(s) 110 include(s) one or more sensors affixed (e.g., taped, attached, glued) externally to a human scalp (e.g., extra-cranial sensor 110-1). For example, extra-cranial sensor 110-1 include(s) an electrode (e.g., electroencephalography (EEG) electrode) or a plurality of electrodes (e.g., electroencephalography (EEG) electrodes) affixed externally to the scalp (e.g., glued to the skin via conductive gel), or more generally positioned at respective positions external to the scalp. Alternatively, dry electrodes can be used in some implementations (e.g., conductive sensors that are mechanically placed against a living subject's body rather implanted within the living subject's body or held in place with a conductive gel). An example of a dry-electrode is a headband with one or more metallic sensors (e.g., electrodes) that is worn by the living subject during use. The signals obtained from an extra-cranial sensor 110-1 are sometimes herein called EEG signals or time-domain EEG signals.

In some embodiments, sensor(s) 110 include(s) a sensor embedded in a particular location of a brain (e.g., intracranial sensor 110-2). For example, intracranial sensor 110-2 is formed (e.g., fabricated) on a needle embedded in a particular location of the brain with one or more sensing elements located along the length and/or circumference of the needle. In some embodiments, a plurality of sensor(s) 110 (e.g., intracranial sensor 110-2) is formed (e.g., fabricated) on a single needle (e.g., 8 instances of sensor(s) 110 or 8 sensing elements are formed on a single needle) embedded in a particular location of a brain. In some embodiments, intracranial sensor 110-2 includes intracranial depth electrodes implanted in the brain at a plurality of locations to monitor electrical activity in the brain at the plurality of locations. In some embodiments, a plurality of sensor(s) 110 (e.g., numbering between 4 and 80 sensors) is embedded across a plurality of regions of interest in the brain. In such embodiments, individual sensors are sensitive to small electrical potential changes caused by neural signaling at corresponding locations in the brain (or in corresponding regions of the brain). In some implementations, the observed signal (e.g., sensor time-domain signal 201, FIG. 2A) obtained from each sensor 110 (e.g., intracranial sensor 110-2) represents the aggregate activity (e.g., corresponding to 10,000 neurons) in a region proximal to the respective sensor (e.g., intracranial sensor 110-2).

In some embodiments, heartbeat pulse sensor(s) 112 are provided to interface with a living subject's heart to obtain (e.g., sense and/or acquire) sensor time-domain signals (e.g., sensor time-domain signal 201, FIG. 2A) corresponding to heart electrical activity. For example, signals (e.g., sensor time-domain signal 201, FIG. 2A) corresponding to heart electrical activity are obtained from a human heart and correspond to electrical signals obtained from a single cardiomyocyte or from a plurality of cardiomyocytes (e.g., a sinoatrial (SA) node of a human subject). In some embodiments, heartbeat pulse sensor(s) 112 include(s) one or more sensing elements affixed (e.g., taped, attached, glued) externally to a human body (e.g., a human subject's chest, abdomen, arm, or leg). For example, heartbeat pulse sensor(s) 112 include(s) an electrode (e.g., electrocardiography (ECG) electrode) or a plurality of electrodes (e.g., electrocardiography (ECG) electrodes) affixed externally to the human body (e.g., glued to the skin via conductive gel), or more generally positioned at respective positions external to the human body. Alternatively, dry electrodes can be used in some implementations (e.g., conductive sensors that are mechanically placed against a human body rather than being implanted within the human body or held in place with a conductive gel). An example of a dry-electrode is a chest strap with one or more metallic sensors (e.g., electrodes) that is worn by the living subject during use. Another example of a dry-electrode is a thumb apparatus or a hand apparatus with one or more metallic sensing elements (e.g., electrodes) that is touched (e.g., with the living subject's thumbs) and/or held onto (e.g., with the living subject's hands) by the living subject during use. The signals obtained from heartbeat pulse sensor(s) 112 are sometimes herein called ECG signals or time-domain ECG signals.

In some embodiments, heartbeat pulse sensor(s) 112 sense voltages corresponding to heart electrical activity. In alternative embodiments, heartbeat pulse sensor(s) 112 sense electrical currents corresponding to heart electrical activity. In some implementations, heartbeat pulse sensor(s) 112 sense differential voltages (e.g., differences in voltage values) between two measurement locations (e.g., between two sensing elements). For example, when a respective heartbeat pulse sensor 112 includes two or more sensing elements (e.g., electrodes) positioned at respective positions external to the human body, the respective heartbeat pulse sensor 112 senses differential voltages between the two or more sensing elements located at the respective positions. In some implementations, a "twelve-lead electrocardiogram" is constructed by referencing each sensing element of a set of sensing elements to one or more other sensing elements to produce a corresponding set of differential voltage signals (e.g., a twelve-lead set of differential voltage signals), each of which is a respective sensor time-domain signal 201, FIG. 2A.

In some embodiments, arrays of sensors (e.g., sensor(s) 110 and/or heartbeat pulse sensor(s) 112, herein sometimes referred to collectively as "sensor(s) 110/112") are designed to produce a plurality of sensor time-domain signals (e.g., sensor time-domain signals 201, FIG. 2A). In some embodiments, sensor time-domain signals (e.g., sensor time-domain signal 201, FIG. 2A) include wideband features including high-gamma bursts in the range of 80-150 Hz. In some embodiments, sensor(s) 110 embedded in a particular location of the brain are additionally configured to dispense medication to localized portions of the brain. In some embodiments, sensor time-domain signals (e.g., sensor time-domain signal 201, FIG. 2A) include frequencies (sometimes called frequency components) below (e.g., lower than or in the lowest ranges of) the human audible frequency-range.

In some implementations, analog front end 120 and/or electrocardiography (ECG) analog front end 122 (herein sometimes referred to collectively as "analog front end(s) 120/122") receives sensor time-domain signals (e.g., sensor time-domain signal 201, FIG. 2A) from sensor(s) 110/112 and optionally pre-processes the sensor time-domain signals to produce filtered sensor time-domain signals (e.g., filtered sensor time-domain signals 207, FIG. 2A). In some embodiments, a separate (e.g., independent) analog front end is provided for interfacing with each of a set of sensor(s) 110/112. In some embodiments, a first analog front end is provided for interfacing with a set of sensor(s) 110, and a second (i.e., distinct) electrocardiography (ECG) analog front end 122 is provided for interfacing with a set of heartbeat pulse sensor(s) 112. In such embodiments, body interface system 100 comprises a plurality of analog front end modules (e.g., analog front end 120-a, analog front end 120-b, analog front end 120-c, etc., and optionally one or more electrocardiography (ECG) analog front end(s) 122) for interfacing with a plurality of sensor(s) 110/112.

As shown in FIG. 1, body interface system 100 includes digital processor system 160 for processing signals obtained from the living subject (e.g., signals corresponding to electrical activity of the brain or heart), optionally after the signals are pre-processed by analog front end 120/122. Digital processor 160 includes signal conditioning module(s) 130/132, signal modulator(s) 140/142, and synthesizer module(s) 150/152. In some embodiments, a separate (e.g., independent) signal conditioning module, a separate (e.g., independent) signal modulator, and/or a separate (e.g., independent) synthesizer module is provided for interfacing with each sensor 110/112 in a set of two or more sensors 110/112 (optionally through a separate analog front end module). In such embodiments, body interface system 100 comprises a plurality of signal conditioning modules (e.g., signal conditioning module 130-*a*, signal conditioning module 130-*b*, signal conditioning module 130-*c*, etc., and optionally one or more signal conditioning module(s) 132), a plurality of signal modulator(s) (e.g., signal modulator(s) 140-*a*, signal modulator(s) 140-*b*, signal modulator(s) 140-*c*, etc., and optionally one or more signal modulator(s) 142), and/or a plurality of synthesizer modules (e.g., synthesizer module 150-*a*, synthesizer module 150-*b*, synthesizer module 150-*c*, etc., and optionally one or more synthesizer modules 152) for interfacing with a plurality of sensors 110/112 and processing signals obtained from those sensors.

In some embodiments, a respective signal conditioning module 130/132 includes a data convertor (e.g., an analog to digital convertor for converting an analog filtered sensor time-domain signal obtained from sensor(s) 110/112 to a corresponding digital representation), an upsampler and a digital low-pass filter. In some implementations, signal modulators 140/142 receive the digitized time-domain signals output by signal conditioning modules 130/132, and concurrently generate a set of acoustic parameters, including a plurality of time-varying acoustic parameters from (e.g., using) the digitized time-domain signals. One or more of the plurality of time-varying acoustic parameters is modulated in accordance with at least the signal value of the time-domain signal (e.g., time-domain signal 218, FIG. 2B, produced by signal conditioning module 130/132). In some embodiments, synthesizer module (e.g., synthesizer module 150/152) combines the concurrently generated set of acoustic parameters to produce a representation of an acoustic signal corresponding to the time-domain signal (e.g., time-domain signal 218, FIG. 2B, produced by signal conditioning module 130/132).

In some embodiments, a plurality of representations of acoustic signals are combined to produce a combined acoustic signal (e.g., combined acoustic signal 240, FIG. 2D). Alternatively, a combined acoustic signal is generated by combining acoustic signals corresponding to the plurality of representations of acoustic signals produced by digital processor system 160. In yet another alternative, a plurality of acoustic signals, each corresponding to one of more of the aforementioned representations of acoustic signals, are recorded on distinct tracks, where the distinct tracks are configured to enable concurrent playback of the acoustic signals recorded in those tracks.

FIG. 2A illustrates a block diagram of an analog front end (e.g., analog front end 120/122, FIG. 1) optionally included in body interface system 100. In some embodiments, analog front end 120/122 receives a sensor time-domain signal (e.g., sensor time-domain signal 201) from a respective sensor 110/112 and pre-processes the sensor time-domain signal to produce a filtered sensor time-domain signal (e.g., filtered sensor time-domain signal 207). When body interface system 100 includes a plurality of analog front ends 120/122, the analog front ends 120/122 process a corresponding number of sensor time-domain signals in parallel to produce filtered sensor time-domain signals.

In some embodiments, analog front end 120/122 includes interface circuitry (e.g., interface analog circuitry 202) to interface with a respective sensor 110/112, for example, by way of providing bias voltages and/or currents to the respective sensor 110/112, buffering signals (e.g., using a buffer amplifier) received from sensor(s) 110/112 and/or providing appropriate coupling conditions (e.g., providing appropriate input impedance) for interfacing with the signals received from sensor(s) 110/112.

Alternatively, or in addition, according to some implementations, analog front end 120/122 includes one or more amplifiers 204 and/or filters 206 to pre-process (e.g., amplify and/or filter) sensor time-domain signals corresponding to brain electrical activity or heart electrical activity (e.g., sensor time-domain signal 201, FIG. 2A) obtained (e.g., sensed and/or acquired) from one or more sensors 110/112. As noted above, in some embodiments, analog front end 120/122 produces a filtered sensor time-domain signal (e.g., filtered sensor time-domain signal 207).

FIG. 2B illustrates a block diagram of a signal conditioning module (e.g., signal conditioning module 130/132) included in body interface system 100. As shown in FIG. 2B, signal conditioning module 130/132 receives filtered sensor time-domain signals (e.g., filtered sensor time-domain signal 207)—optionally obtained after pre-processing by analog front end 120/122—and conditions the filtered sensor time-domain signals to produce time-domain signals (e.g., time-domain signal 218).

In some embodiments, the signal conditioning module (e.g., signal conditioning module 130/132) includes a data convertor (e.g., analog to digital convertor 208) for converting an analog filtered sensor time-domain signal obtained from sensor(s) 110/112 (optionally after pre-processing by analog front end 120/122) to a corresponding digital representation with a predefined sampling rate (e.g., a sampling rate between 500 Hz and 2 kHz, such as 500 Hz; or more generally a sampling rate between 400 Hz to 4 kHz). Signal conditioning module 130/132 includes an upsampler (e.g., upsampler 212) to upsample (e.g., increase the sampling rate of) the digital representation of the analog filtered sensor time-domain signal to produce a first intermediate signal (e.g., first intermediate signal 214). In some embodiments, the digital representation of the analog filtered sensor time-domain signal is upsampled to produce a first intermediate signal having an audio sampling rate, for example, an sampling rate (e.g., 48 kHz) used in conventional audio applications. In some implementations, the first intermediate signal (e.g., first intermediate signal 214) produced by upsampler 212 has a sampling rate of 48 kHz.

In some implementations, signal conditioning module 130/132 includes one or more digital low-pass filters (e.g., digital low pass filter(s) 216) for filtering first intermediate signal 214 so as to produce time-domain signal 218. In some implementations, digital low pass filter(s) 216 is a second order low-pass Butterworth filter with a 250 Hz corner frequency. Digital low pass filter(s) 216 filter(s) first intermediate signal 214 to produce time-domain signal 218. In some embodiments, upsampler 212 and digital low pass filter(s) 216 are implemented in digital signal processor 210, sometimes called a DSP. In some other implementations, upsampler 212 and digital low pass filter(s) 216 are implemented in circuitry. Alternatively, upsampler 212 and digital low pass filter(s) 216 are implemented in software executed by a general purpose processor. Without limitation, it is noted that upsampling and then low pass filtering the digital representation of the analog filtered sensor time-domain signal may be used to convert the output of one or more sensors (e.g., inter-cranial or extra-cranial sensors and/or heartbeat/pulse sensors) to a form that is suitable for use with a music or other audio synthesizer, while removing or limiting artifacts produces by the conversion process.

FIG. 2C illustrates a block diagram of signal modulators 140/142 and synthesizer module 150/152. Signal modulators 140/142 receive time-domain signal 218 from signal conditioning module 130/132 (as explained above with reference to FIG. 2B). Signal modulators 140/142 concurrently generate a set of acoustic parameters, including a plurality of time-varying acoustic parameters. In some embodiments, the plurality of acoustic parameters include a frequency-control parameter (e.g., frequency-control parameter 222-a). In some embodiments, the plurality of acoustic parameters includes a vowel-control parameter (e.g., vowel-control parameter 222-b). In some embodiments, the plurality of acoustic parameters includes a time-varying intensity-control parameter (e.g., intensity-control parameter 222-c). In some embodiments, the set of acoustic parameters includes a pitch-control parameter (e.g., pitch-control parameter 222-d). In some embodiments, the set of acoustic parameters includes one or more sonic identity parameters (e.g., sonic identity parameter(s) 222-e).

In some embodiments, signal modulator(s) 140/142 include(s) a vibrato modulator (e.g., vibrato modulator 220-a) which generates a vibrato or frequency-control parameter (e.g., frequency-control parameter 222-a). In some implementations, the vibrato modulator (e.g., vibrato modulator 220-a) obtains a base frequency or pitch (e.g., a base frequency such as 50 Hz, 100 Hz, or any suitable frequency in the range of 50 Hz to 4 kHz) and modulates the base frequency in accordance with the signal value (e.g., amplitude, intensity and/or power) of the time-domain signal (e.g., time-domain signal 218). In other implementations, the vibrato modulator generates a vibrato or frequency-control parameter in accordance with the signal value of the time-domain signal (e.g., time-domain signal 218) that does not incorporate the base frequency or pitch. The amount of vibrato, as represented by the vibrato or frequency-control parameter, controls variations in frequency in the synthesized audio signal (i.e., the representation of an acoustic signal corresponding to the time-domain signal).

In some embodiments, signal modulator(s) 140/142 include(s) a vowel modulator (e.g., vowel modulator 220-b) which generates a vowel-control parameter (e.g., vowel-control parameter 222-b). In some implementations, a vowel modulator (e.g., vowel modulator 220-b) selects a sequence of acoustic waveform patterns from a set of N (e.g., N is an integer in the range of 2 to 15, such as N=12) acoustic waveform patterns comprising a sequence of phoneme waveform patterns (e.g., phoneme patterns corresponding to sounds in spoken language). In some implementations, the phoneme patterns include a plurality of vowel waveform patterns, and optionally include phoneme patterns (e.g., "sss" or "vvv") that are not vowel waveform patterns. In some implementations, each of the phoneme patterns is distinguished from the other phoneme waveform patterns in the set with respect to acoustic characteristics such as formants. In some embodiments, vowel modulator (e.g., vowel modulator 220-b) modulates a rate at which the acoustic waveform (e.g., vowel waveform) patterns are sequentially selected in accordance with the signal value (e.g., amplitude, intensity and/or power) of the time-domain signal. For example, vowel modulator (e.g., vowel-control parameter 222-b) modulates a rate at which acoustic waveform patterns from a set of 12 acoustic waveform patterns are sequentially selected in accordance with the signal value (e.g., amplitude) of the time-domain signal (e.g., time-domain signal 218). For example, an increase in signal value (e.g., amplitude) of the time-domain signal (e.g., time-domain signal 218), causes vowel modulator (e.g., vowel-control parameter 222-b) to sequentially select acoustic waveform patterns from a set of 12 acoustic waveform patterns more rapidly or at an increased rate; and conversely, a decrease in signal value (e.g., amplitude) of the time-domain signal (e.g., time-domain signal 218), causes vowel modulator (e.g., vowel-control parameter 222-b) to sequentially select acoustic waveform patterns from a set of 12 acoustic waveform patterns more gradually (e.g., slowly) or at a decreased rate.

In some embodiments, signal modulator(s) 140/142 include(s) an intensity modulator (e.g., intensity modulator 220-c) which generates an intensity-control parameter (e.g., intensity-control parameter 222-c). For example, an intensity modulator (e.g., intensity modulator 220-c) computes a time-varying amplitude value in accordance with the signal value (e.g., amplitude, intensity and/or power) of the time-domain signal (e.g., time-domain signal 218) and generates a time-varying intensity-control parameter (e.g., intensity-control parameter 222-c) corresponding to the computed time-varying amplitude value. In some implementations, an increase in signal value (e.g., amplitude) of the time-domain signal (e.g., time-domain signal 218), causes the time-varying amplitude value—and corresponding time-varying intensity-control parameter (e.g., intensity-control parameter 222-c)—computed by intensity modulator (e.g., intensity modulator 220-c) to increase. Conversely, a decrease in signal value of the time-domain signal (e.g., time-domain signal 218), causes the time-varying amplitude value—and corresponding time-varying intensity-control parameter (e.g., intensity-control parameter 222-c)—computed by intensity modulator (e.g., intensity modulator 220-c) to decrease.

In some embodiments, signal modulator(s) 140/142 include(s) a pitch modulator (e.g., pitch modulator 220-d) which generates a pitch-control parameter (e.g., pitch-control parameter 222-d). In some embodiments, pitch modulator (e.g., pitch modulator 220-d) selects a base frequency (e.g., corresponding to an acoustic pitch) in accordance with a spatial location of sensing the time-domain signal. In some embodiments, pitch modulator (e.g., pitch modulator 220-d) generates a time-varying pitch-control parameter in accordance with the selected base frequency and the signal value (e.g., amplitude, intensity and/or power) of the time-domain signal (e.g., time-domain signal 218, FIG. 2B). For example, pitch modulator (e.g., pitch modulator 220-d) selects a base frequency (e.g., a pitch) in accordance with a spatial location in the brain of sensing (e.g., by way of sensor(s) 110/112 located at different spatial locations in the brain) of the time-domain signal (e.g., sensor time-domain signal 201, FIG. 2A). For example, for a time-domain signal obtained from the left hemisphere in the brain, pitch modulator (e.g., pitch modulator 220-d) selects a lower base frequency (e.g., a frequency corresponding to the pitch of baritone voice); for a time-domain signal obtained from the right hemisphere in the brain, pitch modulator (e.g., pitch modulator 220-d) selects a higher base frequency (e.g., a frequency corresponding to the pitch of a tenor voice); and for a time-domain signal obtained from the heart, pitch modulator (e.g., pitch modulator 220-d) selects a still higher base frequency (e.g., a frequency corresponding to the pitch of soprano voice). More generally, in some implementations, when more than one time-domain signal is obtained from distinct sensors on a human body (e.g., distinct intracranial sensors in the brain, distinct extra-cranial sensors, and/or distinct ECG sensors), each time-domain signal is assigned a distinct base frequency so as to enable a listener to distinguish between the "voices" (acoustic signals or acoustic signal portions) corresponding to the distinct sensors and their time-domain signals.

In some embodiments, signal modulator(s) 140/142 generates, obtains or otherwise provides one or more sonic identity parameters 222-e. In some embodiments, signal modulator(s) 140/142 select(s) a sonic identity (for example, specific defining acoustic characteristics; e.g., acoustic characteristics associated with specific musical instruments) in accordance with a respective time-domain signal (e.g., a time-domain signal corresponding to a spatial location in the brain of sensing or a spatial location in the heart of sensing by way of sensors 110/112 located at different spatial locations in the brain and heart, respectively) and generates, obtains or otherwise provides one or more sonic identity parameter 222-e in accordance with the selected sonic identity. For example, for a time-domain signal obtained from the left hemisphere in the brain, a signal modulator(s) 140 selects a sonic identity corresponding to the sonic identity of (e.g., acoustic characteristics defining or associated with) a violin; for a time-domain signal obtained from the right hemisphere in the brain, a signal modulator(s) 140 selects a sonic identity corresponding to the sonic identity of (e.g., acoustic characteristics defining or associated with) a guitar; and for a time-domain signal obtained from the heart, a signal modulator(s) 142 selects a sonic identity corresponding to the sonic identity of (e.g., acoustic characteristics defining or associated with) a clarinet. More generally, in some implementations, when more than one time-domain signal is obtained from distinct sensors on a human body (e.g., from distinct intracranial sensors in the brain, or from distinct extra-cranial sensors, or from distinct ECG sensors), each time-domain signal is assigned a distinct sonic identity (e.g., and a corresponding set of one or more sonic identity parameters 222-e), so as to enable a listener to distinguish between the "voices" (acoustic signals or acoustic signal portions) corresponding to the distinct sensors and their time-domain signals.

One or more of the plurality of time-varying acoustic parameters (e.g., frequency-control parameter 222-a, vowel-control parameter 222-b, and/or intensity-control parameter 222-c) is modulated in accordance with at least the signal value (e.g., amplitude, intensity, and/or power) of the time-domain signal (e.g., time-domain signal 218, FIG. 2B, produced by signal conditioning module 130/132).

A synthesizer module (e.g., synthesizer module 150/152) combines the concurrently generated set of acoustic parameters (e.g., the acoustic parameters produced by signal modulator(s) 140/142 described above) to produce a representation of an acoustic signal (e.g., representation of acoustic signal 230) corresponding to the time-domain signal (e.g., time-domain signal 218, FIG. 2B, produced by signal conditioning module 130/132). In some embodiments, synthesizer module 150/152 is a music synthesizer or a music synthesizer module, for example a frequency modulation synthesizer (e.g., frequency modulation synthesizer 224). In some embodiments, a frequency modulation synthesizer (e.g., frequency modulation synthesizer 224) uses frequency modulation synthesis, controlled by the concurrently generated set of acoustic parameters, to generate a representation of an acoustic signal 230. For example, the frequency modulation synthesizer (e.g., frequency modulation synthesizer 224) modifies the timbre (e.g., the quality) of a waveform by frequency modulating it with a modulating signal. With respect to frequency modulation synthesis, U.S. Pat. No. 4,018,121, "Method of synthesizing a musical sound" is hereby incorporated by reference in its entirety.

As shown in FIG. 2D, in some embodiments, a plurality of representations of acoustic signals 230 (e.g., representation of acoustic signal 230-a, 230-b, 230-c, 230-d, and 230-e) are passed to a combiner module 170 and are combined using a summing unit 175 (e.g., a summing amplifier or a software implementation thereof) to produce a combined acoustic signal 240. In some embodiments, combiner module 170 includes one or more sub-modules configured to perform post-processing of the plurality of representations of acoustic signals 230 (e.g., respectively weighting of each of the plurality of representations of acoustic signals) or of the combined acoustic signal 240 (e.g., compression, equalization, etc.).

As shown in FIG. 1, in some embodiments, signal modulator 140/142 and/or synthesizer module 150/152 are implemented in digital processor 160. In some implementations, signal modulator 140/142 and/or synthesizer module 150/152 are implemented in a digital signal processor, sometimes called a DSP. In some implementations, signal modulator 140/142 and/or synthesizer module 150/152 are implemented in circuitry. And in some implementations, signal modulator 140/142 and/or synthesizer module 150/152 are implemented in software executed by a general purpose processor.

FIG. 3 is a block diagram illustrating digital processor system 160 in accordance with some embodiments. Digital processor system 160 typically includes one or more processing units (CPU's) 302 for executing modules, programs and/or instructions stored in memory 310 and thereby performing processing operations; one or more network or other communications interfaces 304; memory 310; and one or more communication buses 309 for interconnecting these components. The communication buses 309 optionally include circuitry (sometimes called a chipset) that interconnects and controls communications between system components. Digital processor system 160 optionally includes a user interface 305 comprising a display 306, one or more input devices 307 (e.g., keyboard, mouse, touch screen, keypads, etc.), and speaker(s) 308 (optionally for audio playback of acoustic signals corresponding to brain and/or heart activity). Digital processor system 160 optionally includes sensor interface(s) 370 for interfacing with sensor(s) 110/112 (FIG. 1) and/or analog front end 120/122 (FIG. 1) and synthesizer module 374 for combining concurrently generated acoustic parameters to produce a representation of an acoustic signal (e.g., representation of acoustic signal 230, FIG. 2C) corresponding to one or more time-domain signals (e.g., time-domain signal 218, FIG. 2B).

Memory 310 includes high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. Memory 310 optionally includes one or more storage devices remotely located from the CPU(s) 302. Memory 310, or alternately the non-volatile memory device(s) within memory 310, comprises a non-transitory computer readable storage medium. In some embodiments, memory 310, or the computer readable storage medium of memory 310 stores the following programs, modules and data structures, or a subset thereof:

Operating system 312 that includes procedures for handling various basic system services and for performing hardware dependent tasks;

Network communication module 314 that is used for connecting digital processor system 160 to other computers via the one or more communication network interfaces 309 (wired or wireless) and one or more communication networks, such as the Internet, other wide area networks, local area networks, metropolitan area networks, and so on;

User interface module 316 that receives commands from the user via one or more input devices 307 of user interface 305, generates user interface objects in display device 306, and optionally generates representations of signals corresponding to brain and/or heart activity, information corresponding to sensor(s) and sensor interfaces, and information related to the configuration of body interface system 100 for display on display device 306;

Parameter controller 320 that controls (e.g., executes instructions for) the generation of the set of acoustic parameters, including a plurality of time-varying acoustic parameters (such as a frequency-control parameter (sometimes called a vibrato parameter), a vowel-control parameter, an intensity-control parameter, a pitch-control parameter, and/or an identity-control parameter). Parameter controller 320 also interacts with sensor interface(s) 370 to facilitate selection of parameters (e.g., any of the aforementioned parameters) and corresponding parameter values based on the sensor(s) selected and sensor signals obtained (e.g., based on a spatial location in the brain and/or heart of sensing the time-domain signal). For example, sensor interface module 318 interfaces with parameter controller 320 to communicate a set of parameters, corresponding to one or more of pitch, vowel selection, vibrato, intensity (amplitude), and sonic identity parameter, selected in accordance the selected sensor, or in accordance with a spatial location in the brain and/or heart of sensing a time-domain signal;

Stored control parameter sets 322 that include one or more sets of signal parameters or values corresponding to signal parameters (for example, one or more values of base frequencies, a set of acoustic waveform patterns corresponding to phoneme patterns, one or more sonic identities, etc.);

Signal conditioning module(s) 130/132 upsamples and low pass filters the sensor time-domain signal to produce a time-domain signal representing brain and/or heart activity;

Signal modulator(s) 140/142 concurrently generate(s) a set of acoustic parameters, including a plurality of time-varying acoustic parameters, for example, a frequency-control parameter (e.g., frequency-control parameter 222-a, FIG. 2C), a vowel-control parameter (e.g., vowel-control parameter 222-b, FIG. 2C), a time-varying intensity-control parameter (e.g., intensity-control parameter 222-c, FIG. 2C), a pitch-control parameter (e.g., pitch-control parameter 222-d, FIG. 2C), and/or an sonic identity parameter (e.g., sonic identity parameter(s) 222-e, FIG. 2C);

Synthesizer module(s) 150/152 combines the concurrently generated set of acoustic parameters to produce a representation of an acoustic signal (e.g., representation of acoustic signal 230, FIG. 2C) corresponding to the time-domain signal (e.g., time-domain signal 218, FIG. 2B, produced by signal conditioning module 130/132);

Combiner Module(s) 170 receive a plurality of representations of acoustic signals (e.g., representation of acoustic signal 230, FIG. 2C) and combine the plurality of representations of acoustic signals to produce a combined acoustic signal (e.g., combined acoustic signal 240, FIG. 2D).

Each of the above identified elements is optionally stored in one or more of the previously mentioned memory devices of digital processor system 160, and corresponds to a set of instructions for performing a function described above. The above identified modules or programs (i.e., sets of instructions) need not be implemented as separate software programs, procedures or modules, and thus various subsets of these modules is optionally combined or otherwise re-arranged in various embodiments. In some embodiments, memory 310 optionally stores a subset of the modules and data structures identified above. Furthermore, memory 310 optionally stores additional modules and data structures not described above.

Although FIG. 3 shows "digital processor system 160," FIG. 3 is intended more as functional description of the various features which are optionally present in a digital processor system than as a structural schematic of the embodiments described herein. In practice, and as recognized by those of ordinary skill in the art, items shown separately could be combined and some items could be separated. For example, some items shown separately in FIG. 3 could be implemented on a single digital processor system and single items could be implemented by one or more digital processor systems. The actual number of digital processor systems used to implement digital processor system 160 and how features are allocated among them will vary from one implementation to another.

Figure 4A:
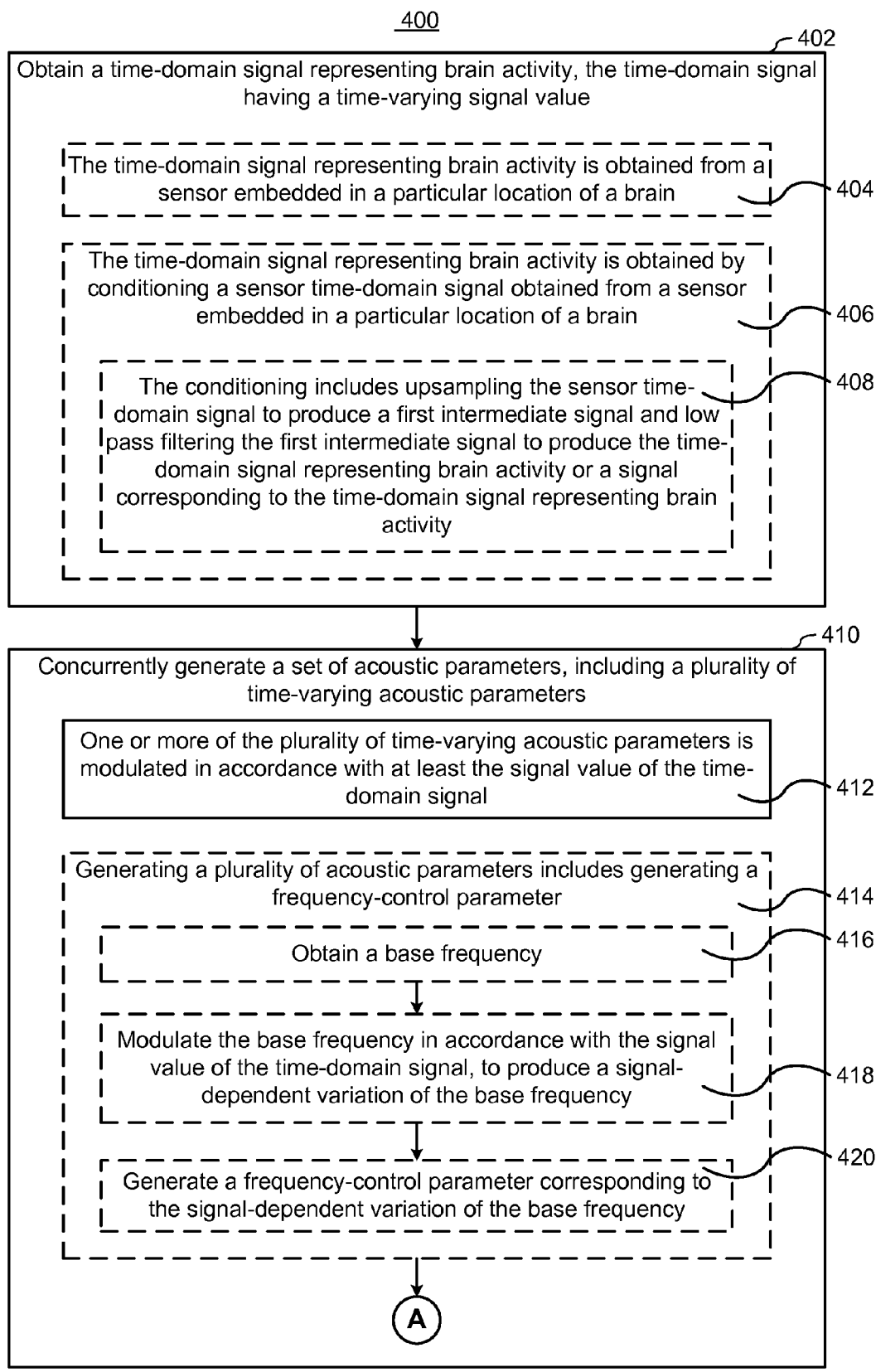
FIGS. 4A-4C include a flow chart illustrating a method for sonifying brain electrical activity, in accordance with some embodiments.
Figure 4B:
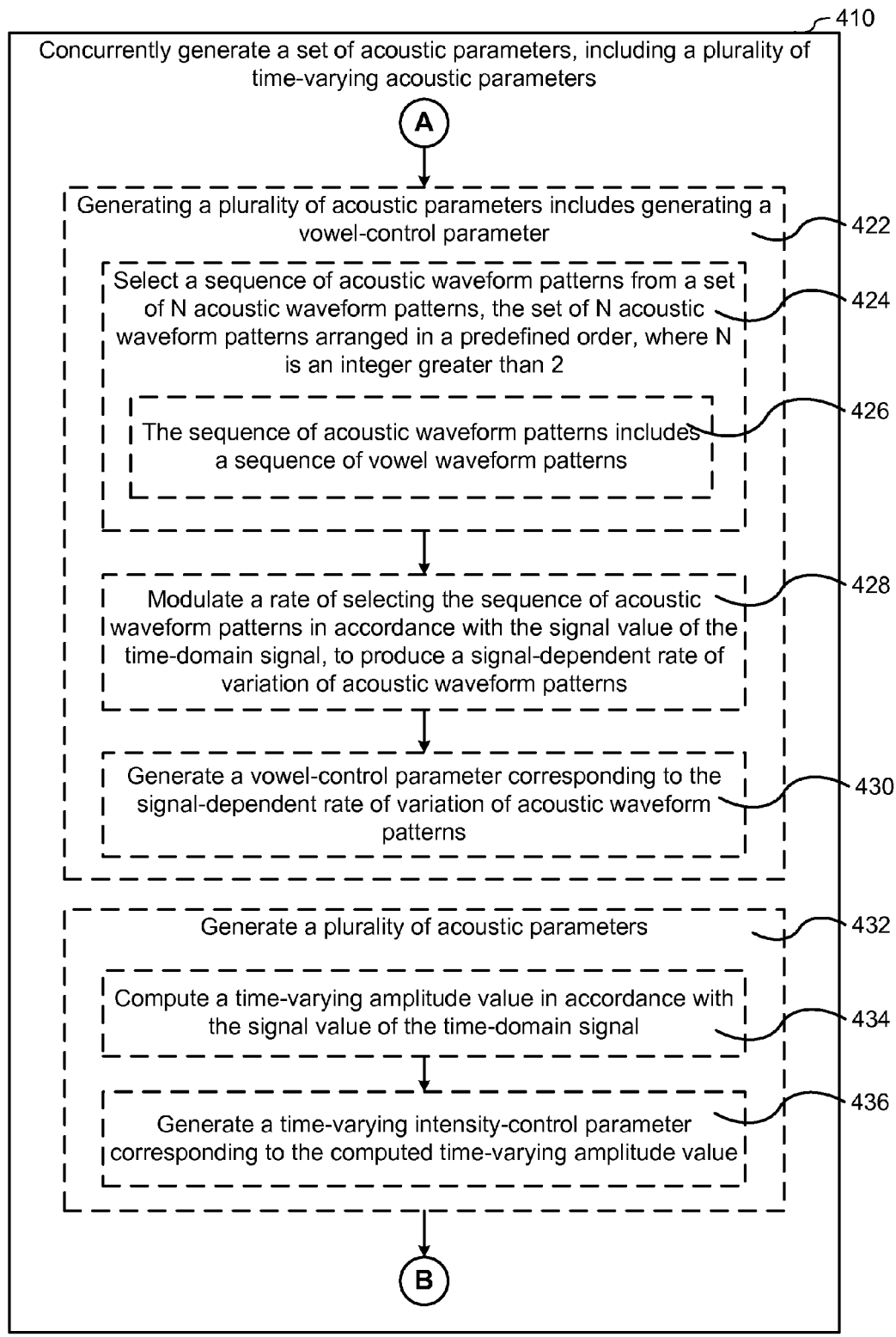
Figure 4C:
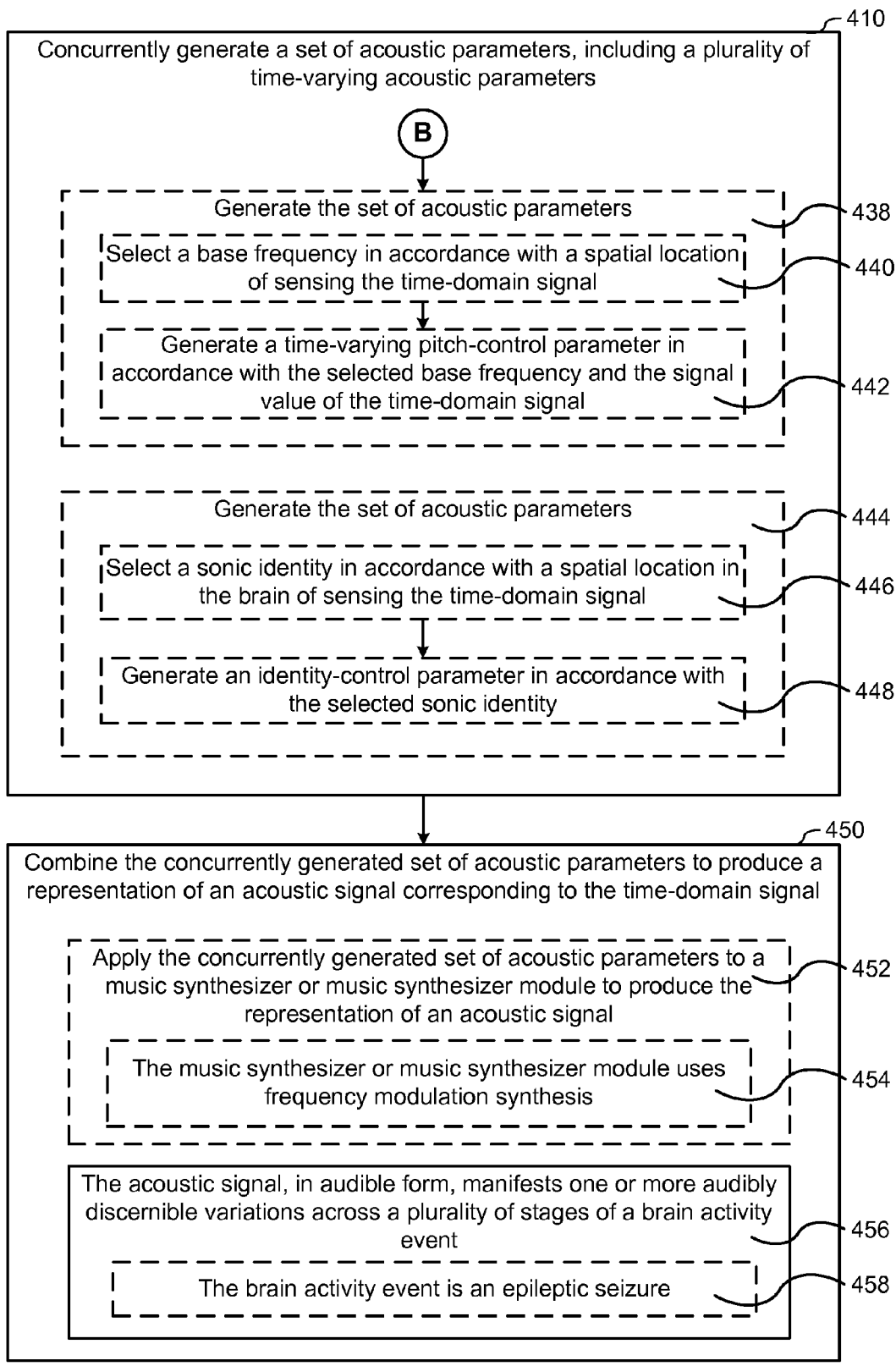

FIG. 4 is a flowchart representing method 400 for sonifying brain electrical activity, according to certain embodiments of the invention. Method 400 is optionally governed by instructions that are stored in a computer readable storage medium and that are executed by a digital processor system (or, optionally, one or more digital processor systems) (e.g., digital processor system 160). Each of the operations shown in FIG. 4 optionally corresponds to instructions stored in a computer memory or computer readable storage medium. The computer readable storage medium optionally includes a magnetic or optical disk storage device, solid state storage devices such as flash memory, or other non-volatile memory device or devices. The computer readable instructions stored on the computer readable storage medium are in source code, assembly language code, object code, or other instruction format that is interpreted by one or more processors.

The digital processor system obtains (402) a time-domain signal (e.g., time-domain signal 218, FIG. 2B) representing brain activity, the time-domain signal having a time-varying signal value. In some embodiments, the time-domain signal representing brain activity is obtained (404) from a sensor embedded in a particular location of a brain. For example, as explained with reference to FIG. 1 and FIG. 2B, time-domain signal 218 (FIG. 2B) is obtained from sensor(s) 110 embedded in a particular location of a brain (e.g., Intracranial Sensor 110-2). In some implementations, intracranial sensor 110-2 is formed (e.g., fabricated) on a needle embedded in the brain with one or more sensing elements located along the length and/or circumference of the needle and differential voltages (e.g., differences in voltage values) are measured between two measurement locations (e.g., between two sensing elements) to produce a differential voltage signal corresponding optionally to sensor time-domain signal 201, FIG. 2a or to time-domain signal 218, FIG. 2B.

In some embodiments, the time-domain signal representing brain activity is obtained (406) by conditioning a sensor time-domain signal obtained from a sensor embedded in a particular location of a brain. For example, as shown in FIG. 1 and FIGS. 2A-2B, sensor time-domain signal 201 is obtained from a sensor embedded in a particular location of a brain (e.g., from intracranial sensor 110-2, FIG. 1) and—after optionally being pre-processed by analog front end 120 to produce filtered sensor time-domain signal 207—is conditioned by signal conditioning module 130.

In some embodiments, the conditioning includes (408) upsampling the sensor time-domain signal to produce a first intermediate signal and low pass filtering the first intermediate signal to produce the time-domain signal representing brain activity or a signal corresponding to the time-domain signal representing brain activity. For example, as shown in FIG. 2B, filtered sensor time-domain signal 207—after conversion from an analog signal to a corresponding digital signal—is upsampled (e.g., by upsampler 212, FIG. 2b) to produce a first intermediate signal (e.g., first intermediate signal 214, FIG. 2B). For example, as explained above, if the original sampling rate of the digital representation of the analog filtered sensor time-domain signal corresponds to 500 Hz, the first intermediate signal (e.g., first intermediate signal 214) produced by upsampler 212 has a sampling rate used in conventional audio applications (e.g., 48 kHz). First intermediate signal 214 is then low pass filtered (e.g., by digital low pass filter(s) 216, FIG. 2b) to produce the time-domain signal representing brain activity or a signal corresponding to the time-domain signal representing brain activity (e.g., time-domain signal 218, FIG. 2B).

The digital processor system concurrently generates (410) a set of acoustic parameters (e.g., see operations 412-448), including a plurality of time-varying acoustic parameters. In this context, parameters are "concurrently generated" even if they are literally generated serially by single-threaded processor, when the resulting parameters are used or applied concurrently for generating an audio signal, or a representation of an audio signal. Typically, two or more concurrently generated parameters are generated or updated in response to a stream of digital signal values corresponding to the time-domain signal.

One or more of the plurality of time-varying acoustic parameters is modulated (412) in accordance with at least the signal value of the time-domain signal. For example, as explained above with reference to FIG. 2C, signal modulator(s) 140 (optionally included in digital processor system 160) concurrently generate(s) a set of acoustic parameters, including a plurality of time-varying acoustic parameters. In some embodiments, as described in relation to FIG. 2C above, the plurality of acoustic parameters includes a vibrato or frequency-control parameter (e.g., frequency-control parameter 222-a), a vowel-control parameter (e.g., vowel-control parameter 222-b), and/or a time-varying amplitude or intensity-control parameter (e.g., intensity-control parameter 222-c). In some embodiments, the set of acoustic parameters includes a pitch-control parameter (e.g., pitch-control parameter 222-d) and/or a sonic identity parameter (e.g., sonic identity parameter 222-e).

In some embodiments, generating a plurality of acoustic parameters includes (414) generating a vibrato or frequency-control parameter (as described herein with respect to operations 416-420). For example, as described above with reference to FIG. 2C, signal modulator(s) 140 (optionally included in a digital processor system) includes vibrato modulator 220-a, which generates frequency-control parameter 222-a.

In some embodiments, the digital processor system obtains (416) a base frequency. In some embodiments, the digital processor system modulates (418) the base frequency in accordance with the signal value of the time-domain signal, to produce a signal-dependent variation of the base frequency. In some embodiments, the digital processor system generates (420) a frequency-control parameter corresponding to the signal-dependent variation of the base frequency. For example, as explained above, vibrato modulator (e.g., Vibrato Modulator 220-a, FIG. 2C) generates a control parameter for controlling the amount of vibrato (which can be considered to be the amount of frequency variation) produced by a music or audio synthesizer. In some implementations (e.g., implementations in which pitch and vibrato are controlled during audio synthesis by separate parameters) the frequency-control parameter is independent of the base frequency or pitch, while in other implementations the frequency-control parameter incorporates the base frequency or pitch.

In some embodiments, generating a plurality of acoustic parameters includes (422) generating a vowel-control parameter (as described herein with respect to operations 424-430). For example, as shown in FIG. 2C, signal modulator(s) 140 (optionally included in digital processor 160) comprise(s) vowel modulator 220-b which generates vowel-control parameter 222-b.

In some embodiments, a digital processor (e.g., digital processor 160) sequentially selects (424) acoustic waveform patterns from a ordered set of N acoustic waveform patterns, the set of N acoustic waveform patterns arranged in a predefined order, where N is an integer greater than 2. In some embodiments, the sequence of selected acoustic waveform patterns includes (426) a sequence of vowel waveform patterns. In some embodiments, a digital processor (e.g., digital processor 160) modulates (428) a rate of sequentially selecting acoustic waveform patterns in accordance with the signal value of the time-domain signal, to produce a signal-dependent rate of variation of acoustic waveform patterns. In some embodiments, a digital processor (e.g., digital processor 160) generates (430) a vowel-control parameter corresponding to the signal-dependent rate of variation of acoustic waveform patterns.

For example, as described above, vowel modulator (e.g., vowel-control parameter 222-b) modulates a rate of sequentially selecting acoustic waveform patterns from a set of 12 acoustic waveform patterns in accordance with the signal value of the time-domain signal (e.g., time-domain signal 218, FIG. 2C). For example, for an increase in signal value of the time-domain signal (e.g., time-domain signal 218), vowel modulator (e.g., vowel-control parameter 222-b) selects (e.g., scans through) a sequence of acoustic waveform patterns from a set of 12 acoustic waveform patterns more rapidly or at an increased rate; conversely, for a decrease in signal value of the time-domain signal (e.g., time-domain signal 218), vowel modulator (e.g., vowel-control parameter 222-b) selects (e.g., scans through) a sequence of acoustic waveform patterns from a set of 12 acoustic waveform patterns more gradually (e.g., slowly) or at a decreased rate.

In some embodiments, the digital processor system generates (432) a plurality of acoustic parameters, as described herein with respect to operations 434-436. In some embodiments, the digital processor system computes (434) a time-varying amplitude value in accordance with the signal value of the time-domain signal. In some embodiments, the digital processor system generates (436) a time-varying intensity-control parameter corresponding to the computed time-varying amplitude value.

For example, as described above in relation to FIG. 2C, an intensity modulator (e.g., intensity modulator 220-c, FIG. 2C) computes a time-varying amplitude value in accordance with the signal value of the time-domain signal (e.g., time-domain signal 218, FIG. 2c) and generates a time-varying intensity-control parameter (e.g., intensity-control parameter 222-c, FIG. 2C) corresponding to the computed time-varying amplitude value. In some implementations, for an increase in signal value of the time-domain signal (e.g., time-domain signal 218), the time-varying amplitude value—and corresponding time-varying intensity-control parameter (e.g., intensity-control parameter 222-c)—computed by intensity modulator (e.g., intensity modulator 220-c) increases. Conversely, for a decrease in signal value of the time-domain signal (e.g., time-domain signal 218), the time-varying amplitude value—and corresponding time-varying intensity-control parameter (e.g., intensity-control parameter 222-c)—computed by intensity modulator (e.g., intensity modulator 220-c) decreases.

In some embodiments, the digital processor system generates (438) the set of acoustic parameters, as described herein with respect to operations 440-442. In some embodiments, the digital processor system selects (440) a base frequency in accordance with a spatial location of sensing the time-domain signal. In some embodiments, the digital processor system generates (442) a time-varying pitch-control parameter in accordance with the signal value of the time-domain signal, and optionally in accordance with the selected base frequency. For example, as shown in FIG. 2C, signal modulator(s) 140 (optionally included in digital processor 160) comprise(s) pitch modulator 220-d which generates pitch-control parameter 222-d in accordance a signal value of the time-domain signal (e.g., time-domain signal 218), and optionally in accordance with a selected base frequency (e.g., corresponding to a spatial location of sensing the time-domain signal).

Without limitation with respect to other implementations, in some implementations the set of acoustic parameters are generated, in accordance with a set of instructions executed by one or more processors of a digital processor system, as described above. The following is an example of a pseudo-code representation of instructions for generating the set of acoustic parameters, once per time period (e.g., once every 10 milliseconds), where SigVal is the signal value for the current time period:

```
// amplitude
amplitude.param = max(0.0, c1 + c2*SigVal);
//pitch
pitch.param = ConvertMidiToFreq(c3 − c4*SigVal);
// vibrato
vibrato-gain.param = pitch.param * (2^c5 − 1);
vibrato.param = vibrato.param + c6*SigVal;
vibrato.freq.param = max(0.0, min(c7, c8+vibrato.param));
//vowel
vow = vow + (c9 * SigVal);
vowel.param = integer ( abs(vow) ) modulo 12;
``` where, in one example, the following coefficient values are used: c1=0.1, c2=20, c3=45, c4=5, c5=0.05, c6=4, c7=8.0, c8=4.5, c9=20. Further, "ConvertMidiToFreq" is a function for converting a midi note to a frequency value, "max" is a function that outputs the maximum of its input values, "min" is a function that outputs the minimum of its input values, "abs" is a function that outputs the absolute value of its input, and "integer" is a function that outputs the integer portion of its input. In another example, in which two or more multiple time-domain signals are processed to produce a corresponding number of audio signals (sometimes called voices for ease of reference), one or more of the coefficients (e.g., c1 to c9 in the above example) are different for different ones of the audio signals, thereby producing audio signals that are audibly distinct. In one example, coefficients c3 (corresponding to base frequency) and c6 (corresponding to amount of vibrato) and c9 (corresponding to rate at which the audio signal traverses a sequence of vowels or phonemes), have different values for each audio signal.

For example, as shown in FIG. 1, Sensor(s) 110 are located at different spatial locations in the brain for sensing the time-domain signal (e.g., Sensor Time-Domain Signal 201), and a base frequency (e.g., a pitch) is selected in accordance with a spatial location in the brain of sensing the time-domain signal. In this example, for a time-domain signal obtained from the left hemisphere in the brain, a lower base frequency (e.g., a frequency corresponding to the pitch of a baritone voice) is selected; whereas for a time-domain signal obtained from the right hemisphere in the brain, a higher base frequency (e.g., a frequency corresponding to the pitch of a tenor voice) is selected.

In some embodiments, the digital processor system generates (444) the set of acoustic parameters, as described with respect to operations 446-448. In some embodiments, the digital processor system selects (446) a sonic identity in accordance with a spatial location in the brain (or, alternatively, on the surface of the cranium) of sensing the time-domain signal. In some embodiments, the digital processor system generates (448) an identity-control parameter in accordance with the selected sonic identity. For example, as shown in FIG. 2C, Signal Modulator(s) 140 (optionally included in Digital Processor 160) comprise(s) Sonic Identity Modulator 220-e which generates Sonic Identity Parameter(s) 222-e in accordance with a selected sonic identity corresponding to a spatial location in the brain of sensing the time-domain signal.

For example, as shown in FIG. 1, Sensor(s) 110 are located at different spatial locations in the brain for sensing the time-domain signal (e.g., Sensor Time-Domain Signal 201), and a sonic identity is selected in accordance with a spatial location in the brain (or, alternatively, on the surface of the cranium) of sensing the time-domain signal. In this example, for a time-domain signal obtained from the left hemisphere in the brain, a sonic identity is selected corresponding to the sonic identity of (e.g., acoustic characteristics defining or associated with) a violin (or a first "voice"); whereas for a time-domain signal obtained from the right hemisphere in the brain, a sonic identity is selected corresponding to the sonic identity of (e.g., acoustic characteristics defining or associated with) a guitar (or as second "voice"). In some implementations, the sonic identity is simply the base frequency of each generated acoustic signal (or representation of an acoustic signal), while in some other implementations, the sonic identity determines both the base frequency and one or more parameters (e.g., multipliers, offsets, etc.) that are used while generating the acoustic parameters corresponding to each time-domain signal (e.g., corresponding to each sensor signal being sonified).

The digital processor system combines (450) the concurrently generated set of acoustic parameters to produce a representation of an acoustic signal corresponding to the time-domain signal. For example, as shown in FIG. 2C, synthesizer module 150 (optionally included in digital processor 160) combines the concurrently generated set of acoustic parameters generated by signal modulator(s) 140 to produce a representation of an acoustic signal (representation of acoustic signal 230) corresponding to the time-domain signal (e.g., time-domain signal 218).

In some embodiments, the digital processor system applies (452) the concurrently generated set of acoustic parameters to a music synthesizer or music synthesizer module to produce the representation of an acoustic signal. In some embodiments, the music synthesizer or music synthesizer module uses (454) frequency modulation synthesis. For example, as shown in FIG. 2C, synthesizer module 150 uses frequency modulation synthesis implemented on frequency modulation synthesizer 224.

The acoustic signal, in audible form, manifests (456) one or more audibly discernible variations across a plurality of stages of a brain activity event. In some embodiments, the brain activity event is (458) an epileptic seizure. For example, the acoustic signal corresponding to representation of acoustic signal 230, in audible form, manifests one or more audibly discernible variations (e.g., variations in vibrato, in rate of change of vowel, and/or in intensity) across a plurality of stages of a brain activity event. In some embodiments in which the brain activity event is an epileptic seizure, the acoustic signal in audible form manifests one or more audibly discernible variations (change in volume, pitch, rate of vowel change) across the stages (e.g., normal state, pre-ictal phase, seizure phase and post-ictal phase) of the epileptic seizure. For example, the acoustic signal is periodic and has higher amplitude during the seizure phase, and is chaotic (has lower or little periodicity) and has lower amplitude during the normal state.

In some implementations, the brain activity event for which brain electrical signals are sonified is not an epileptic seizure, and instead is a respective brain activity event that is the subject of analysis or monitoring. For example, in some implementations the brain activity event for which brain electrical signals are sonified comprises brain activity while the human subject performs various tasks (e.g., mental tasks, physical tasks, operating an apparatus, answering questions, playing a musical instrument, taking an exam, performing or attempting to perform multiple tasks or functions concurrently, etc.), brain activity associated with experiencing various external stimuli, brain activity associated with physiological functions, brain activity associated with various diseases, and the like.

Figure 5:
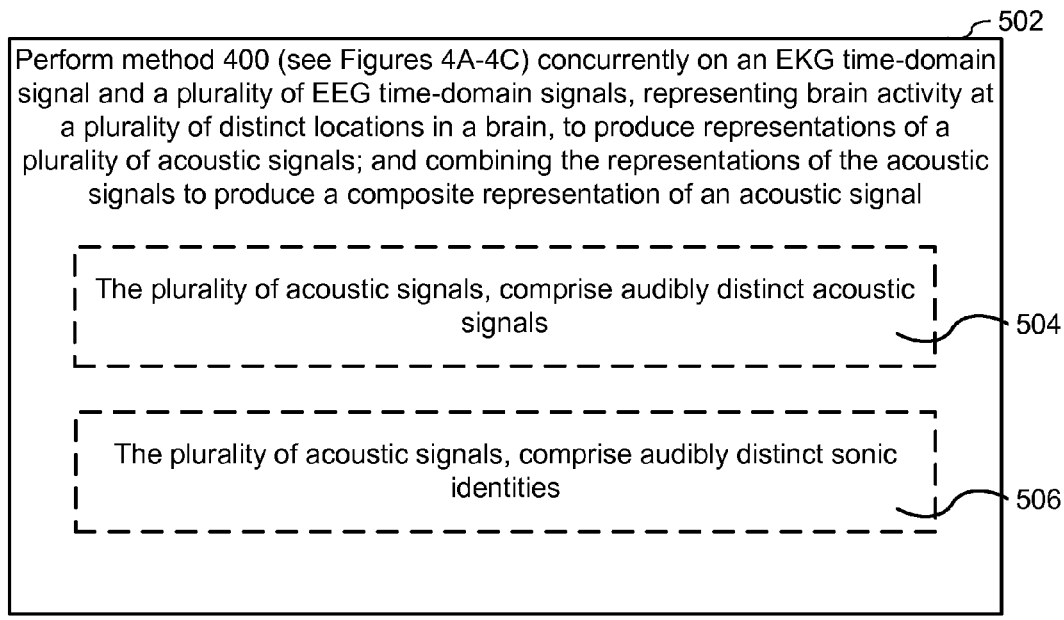
FIG. 5 includes a flow chart illustrating a method for sonifying brain electrical signals concurrently obtained from a plurality of distinct locations in the brain, in accordance with some embodiments.
Figure 6B:
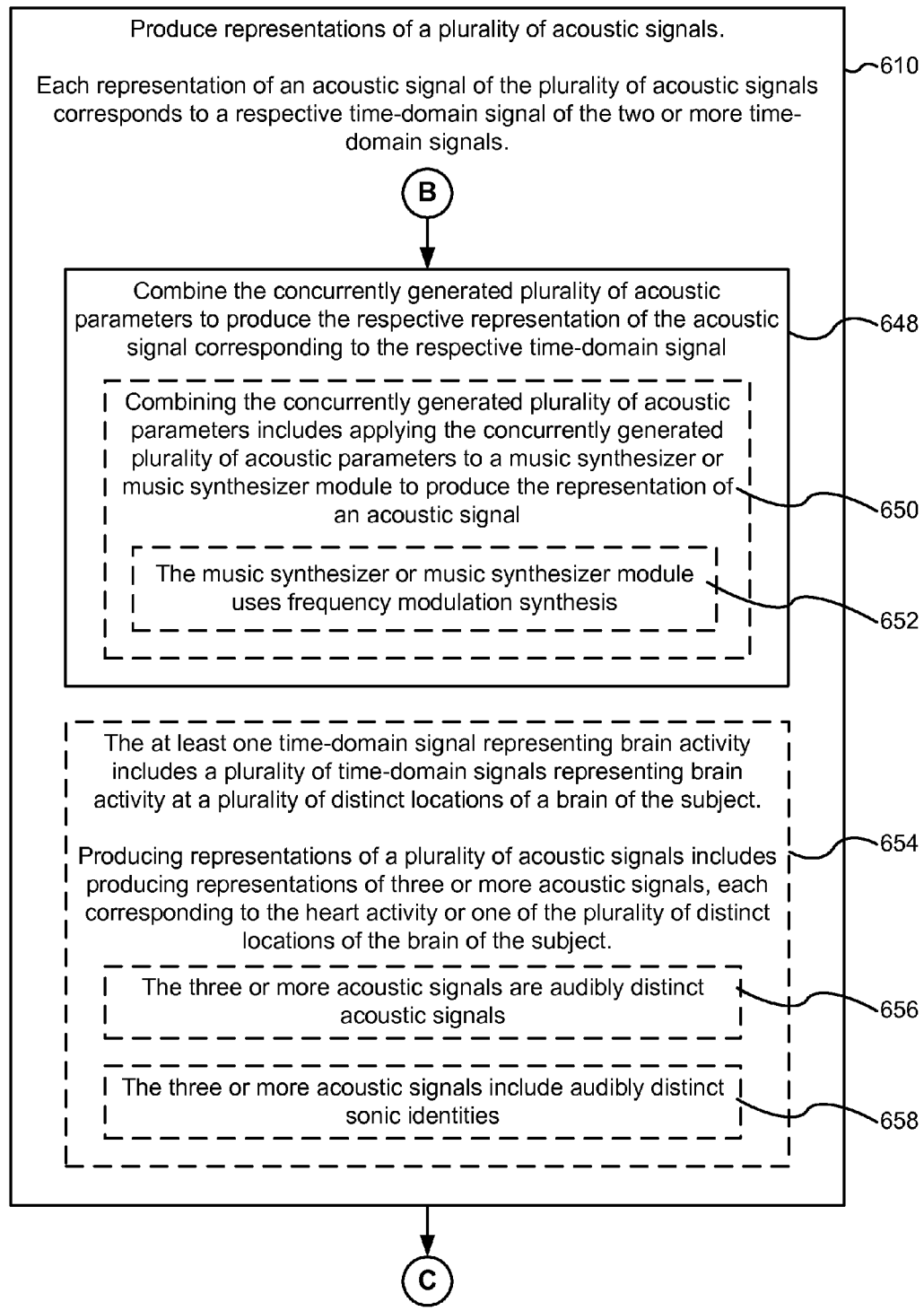
Figure 6C:
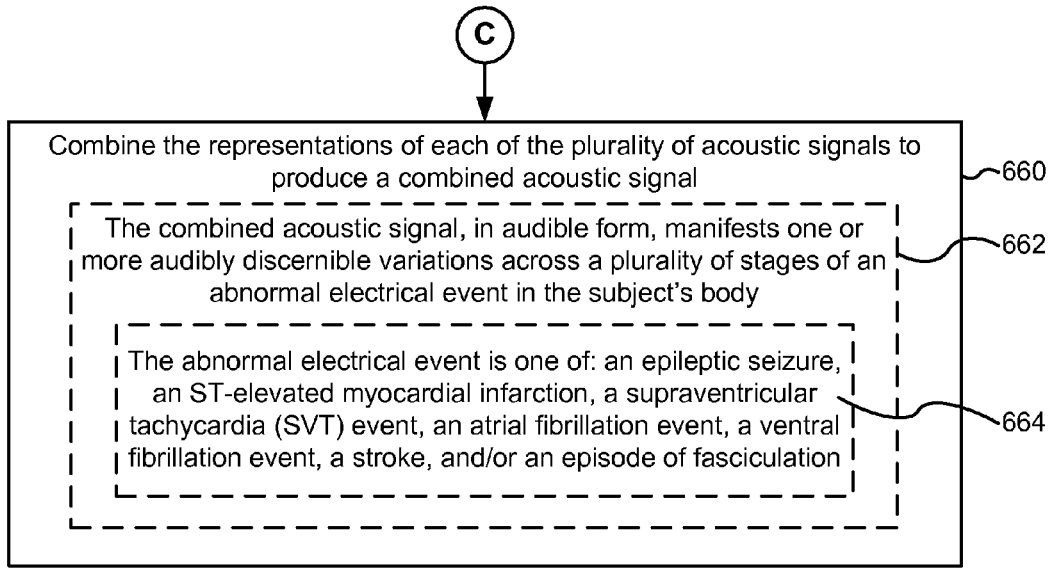
Figure 6D:
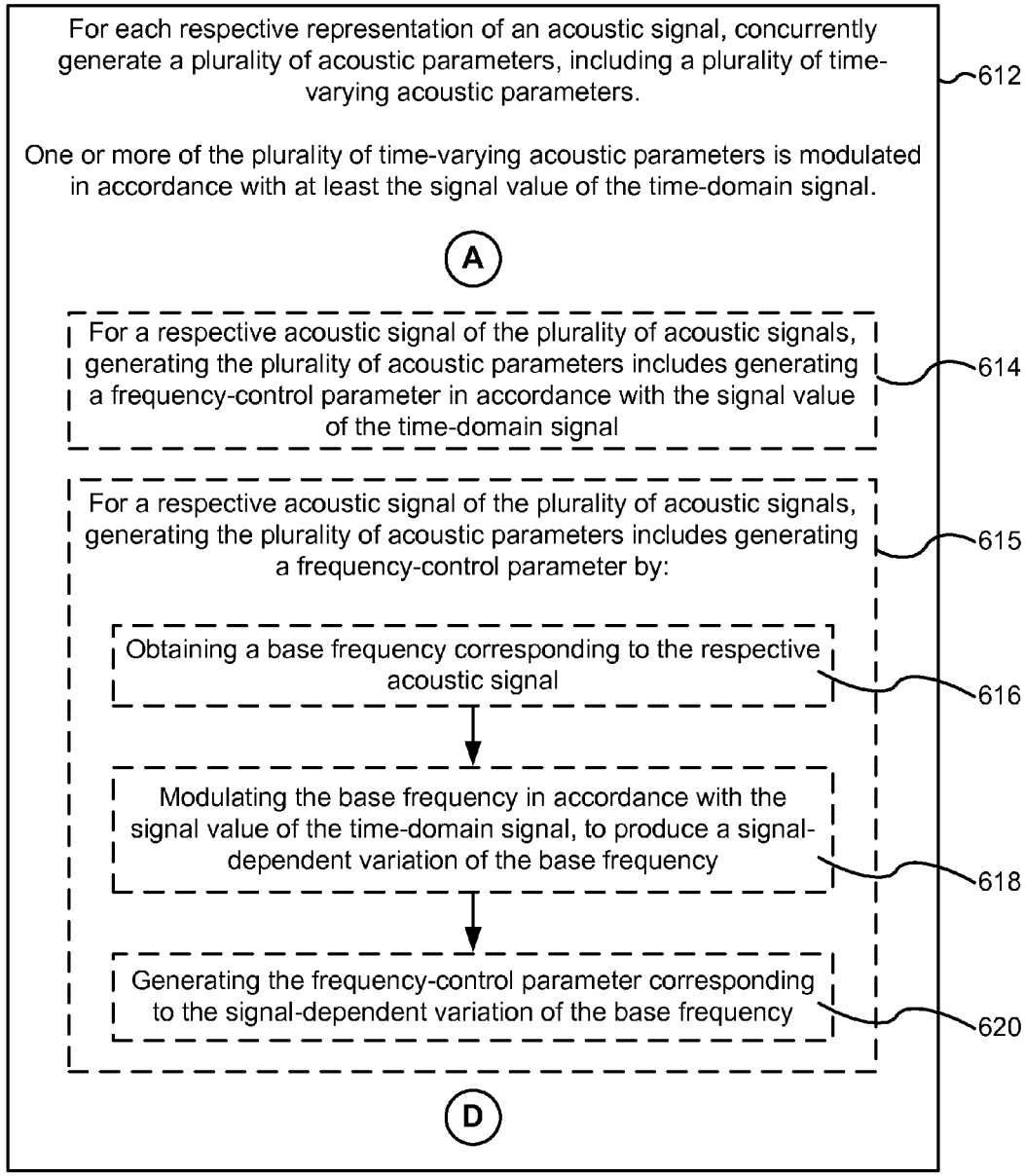
Figure 6E:
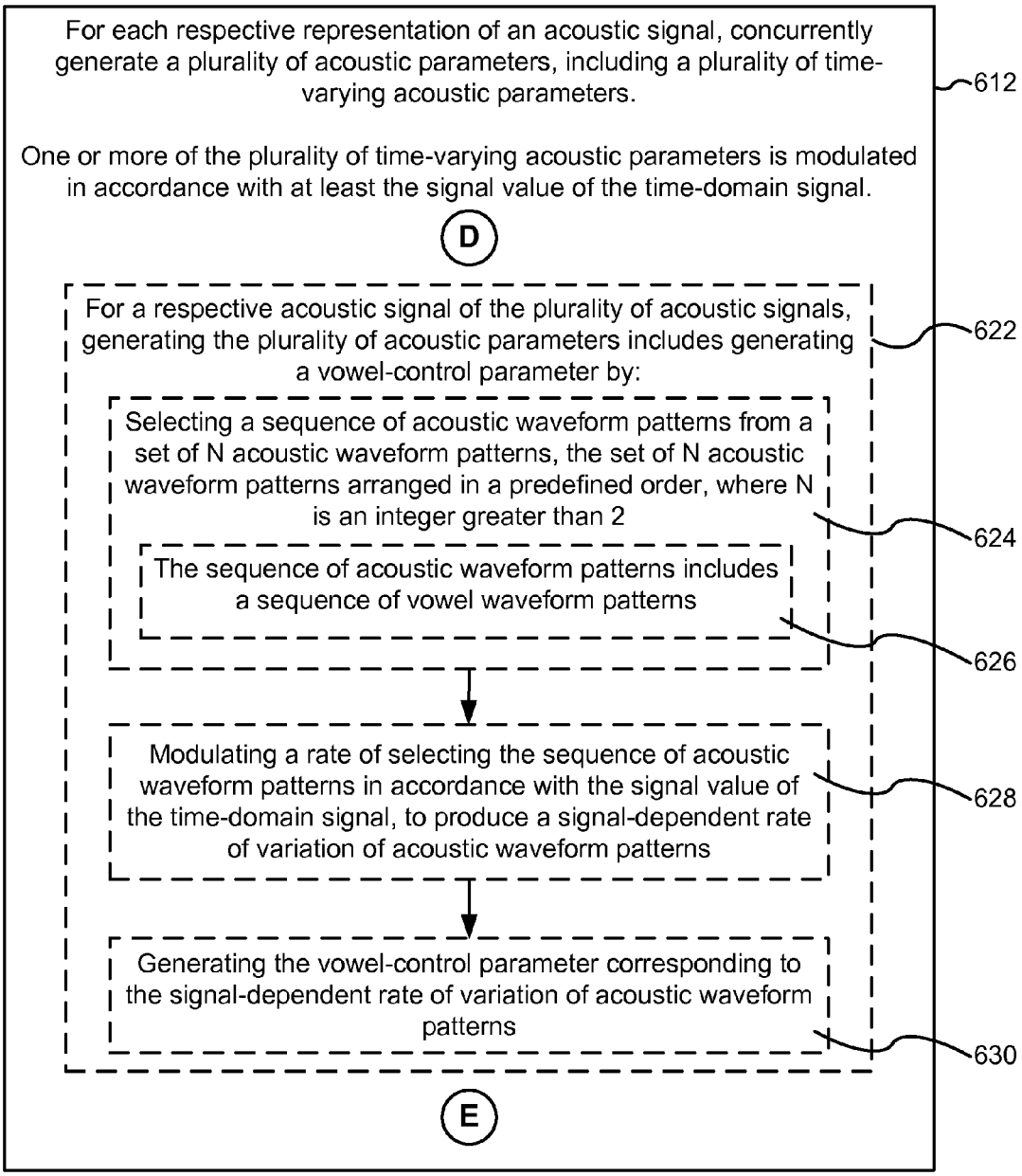
Figure 6F:
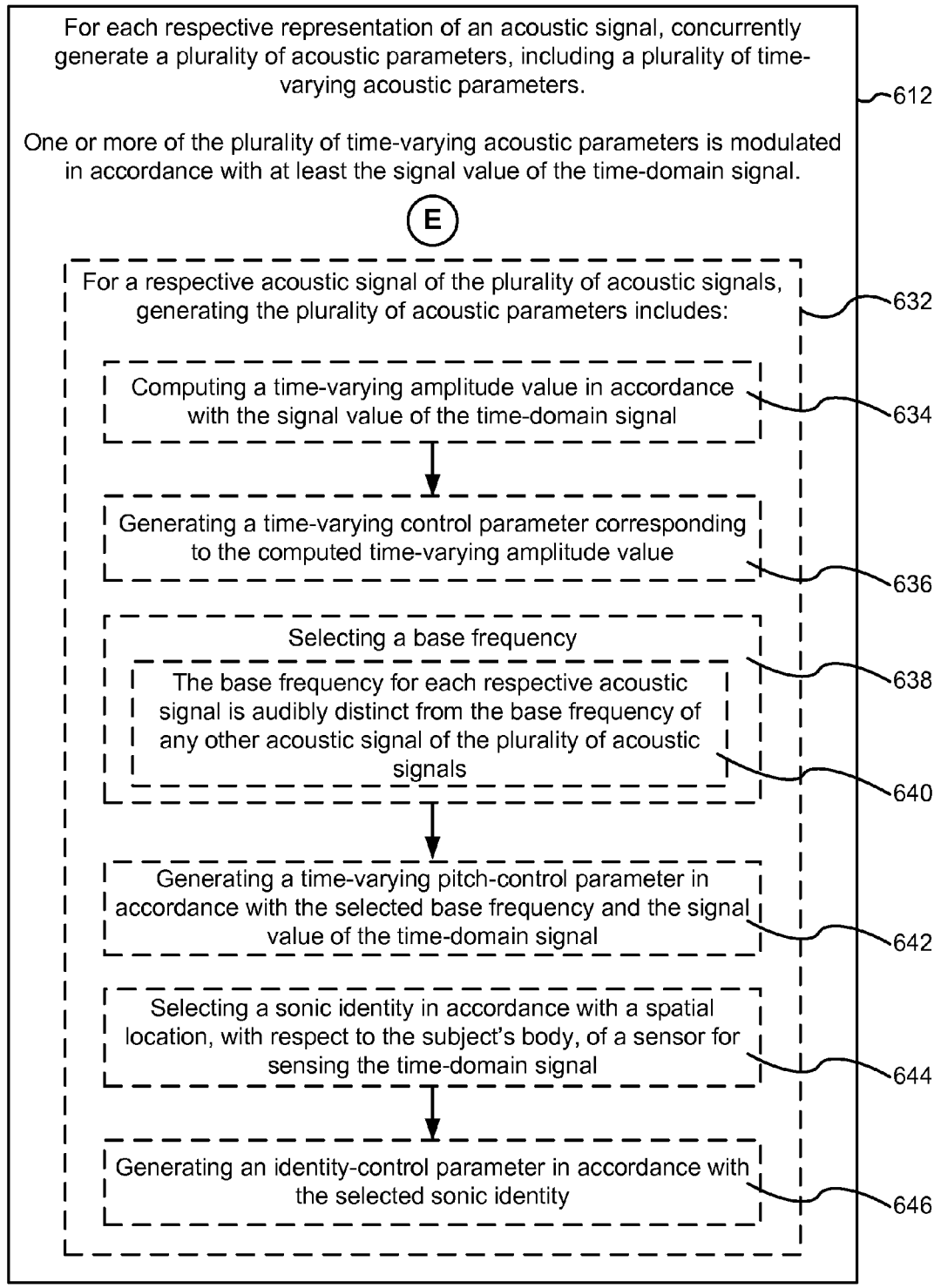

FIG. 5 is a flowchart representing method 500 for sonifying brain electrical signals concurrently obtained from a plurality of distinct locations in the brain, according to certain embodiments of the invention. Method 500 is optionally governed by instructions that are stored in a computer readable storage medium and that are executed by one or more processors of one or more digital processor systems. Each of the operations shown in FIG. 5 optionally corresponds to instructions stored in a computer memory or computer readable storage medium. The computer readable storage medium optionally includes a magnetic or optical disk storage device, solid state storage devices such as Flash memory, or other non-volatile memory device or devices. The computer readable instructions stored on the computer readable storage medium are in source code, assembly language code, object code, or other instruction format that is interpreted by one or more processors.

In some implementations, the digital processor system (e.g., digital processor 160, FIG. 1 and FIG. 3) performs (502) method 400 (described herein with reference to FIGS. 4A-4C) concurrently on a plurality of time-domain signals representing brain activity at a plurality of distinct locations in a brain to produce representations of a plurality of acoustic signals, each corresponding to one of the plurality of distinct locations in the brain. For example, as shown in FIG. 1, digital processor 160 (FIG. 1 and FIG. 3) performs the above-described method 400 concurrently on a plurality of time-domain signals (e.g., a plurality of sensor time-domain signal(s) 201, FIG. 2c, obtained from a plurality of sensor(s) 110, FIG. 1) representing brain activity at a plurality of distinct locations in a brain to produce representations of a plurality of acoustic signals (e.g., a plurality of representation of acoustic signal 230, FIG. 2C). In some embodiments, sensor(s) 110 (e.g., intracranial sensor 110-2), FIG. 1 include intracranial depth electrodes implanted in the brain at a plurality of locations to monitor electrical activity in the brain at the plurality of locations. In such implementations, the observed signal (e.g., sensor time-domain signal 201, FIG. 2a) obtained from each of sensor(s) 110 (e.g., intracranial sensor 110-2) represents the aggregate activity (e.g., corresponding to 10,000 neurons) in the region proximate to the respective sensor (e.g., intracranial sensor 110-2). In some embodiments, arrays of sensors (e.g., sensor(s) 110) are designed to produce a plurality of sensor time-domain signals (e.g., sensor time-domain signal 201, FIG. 2A). In such embodiments, each of the plurality of time-domain signals is normalized (e.g., normalized with respect to signal amplitude or power) and/or offset (e.g., by the addition or subtraction of a fixed signal value) relative to other time-domain signals in the plurality of time-domain signals. Statistical features of the plurality of time-domain signals, for example, obtained from arrays of sensors (e.g., Sensor(s) 110) are optionally used to enhance acoustic characteristics of the representations of a plurality of acoustic signals. For example, in some embodiments, an estimate of the "busiest" signal(s) (e.g., signals with the highest signal content) of the plurality of time domain signals (e.g., obtained from arrays of sensors (e.g., sensor(s) 110) at a plurality of distinct locations in a brain) is computed based on activity detected or computed using a sliding window Fourier transform. In such embodiments, the "busiest" signal(s) are used for method 400 (described herein with reference to FIGS. 4A-4C).

In some embodiments, the plurality of acoustic signals, each corresponding to one of the plurality of distinct locations in the brain (or, alternatively, to a particular sensor or set of sensors 110), comprise (504) audibly distinct acoustic signals. For example, the plurality of acoustic signals, each corresponding to one of the plurality of distinct locations in the brain, comprise audibly distinct pitch (e.g., base frequencies), different rates of vowel transition, different vibrato modulations, and/or different acoustic signal intensities (e.g., loudness of the acoustic signal). In some embodiments, the plurality of acoustic signals, each corresponding to one of the plurality of distinct locations in the brain, comprise (506) audibly distinct sonic identities. For example, as explained above, for a time-domain signal obtained from the left hemisphere in the brain, a sonic identity is selected corresponding to the sonic identity of (e.g., acoustic characteristics defining or associated with) a violin (or, more generally, a first "voice"); whereas for a time-domain signal obtained from the right hemisphere in the brain, a sonic identity is selected corresponding to the sonic identity of (e.g., acoustic characteristics defining or associated with) a guitar (or, more generally, a second "voice").

FIGS. 6A-6F are a flowchart representing a method 600 for sonifying electrical signals obtained from a living subject, in accordance with some embodiments. Method 600 is optionally governed by instructions that are stored in a computer readable storage medium and that are executed by a digital processor system (or, optionally, one or more digital processor systems) (e.g., digital processor system 160). Each of the operations shown in FIGS. 6A-6F optionally corresponds to instructions stored in a computer memory or non-transitory computer readable storage medium. The computer readable storage medium optionally includes a magnetic or optical disk storage device, solid state storage devices such as flash memory, or other non-volatile memory device or devices. The computer readable instructions stored on the non-transitory computer readable storage medium are in source code, assembly language code, object code, or other instruction format that is interpreted by one or more processors. For ease of explanation only, each of the operations shown in FIGS. 6A-6F is described as being executed by a digital processor system (e.g., digital processor 160, FIG. 1).

The digital processor system obtains (602) two or more time-domain signals, including at least one time-domain signal representing brain activity (e.g., electrical activity in the living subject's brain) and at least one time-domain signal representing heart activity (e.g., electrical activity in the living subject's heart), each of the one or more time-domain signals having a time-varying signal value. For example, at least one time-domain signal 218 (FIG. 2B) representing brain activity is obtained from a sensor 110 (FIG. 1) and at least one time-domain signal 218 (FIG. 2B) representing heart activity is obtained from a heartbeat/pulse sensor 112. In some embodiments, a sensor 110 (FIG. 1) and/or a heartbeat/pulse sensor 112 (FIG. 1) includes two or more sensing elements, and the corresponding time-domain signals 218 (FIG. 2B) each comprise a differential voltage signal between two of the two or more sensing elements.

In some embodiments, the at least one time-domain signal representing brain activity is obtained by conditioning (604) a sensor time-domain signal obtained from a sensor embedded in a particular location of a brain. For example, as shown in FIG. 1 and FIGS. 2A-2B, sensor time-domain signal 201 is sometimes obtained from a sensor embedded in a particular location of a brain (e.g., from intracranial sensor 110-2, FIG. 1) and—after optionally being pre-processed by analog front end 120/122 to produce filtered sensor time-domain signal 207—is conditioned by signal conditioning module 130/132.

Alternatively, in some embodiments, the at least one time-domain signal representing brain activity is obtained by conditioning (606) a first sensor time-domain signal obtained from a first dry-contact sensor; and the at least one time-domain signal representing heart activity is obtained by conditioning a second sensor time-domain signal obtained from a second dry-contact sensor. For example, as described with reference to FIG. 1 and FIGS. 2A-2B, a first sensor time-domain signal 201 (e.g., the first sensor time-domain signal) is sometimes obtained from a headband (e.g., the first dry-contact sensor is a headband or is embedded in a headband) with one or more metallic sensors (e.g., electrodes) that is worn by the living subject during use. A second sensor time-domain signal 201 (e.g., the second sensor time-domain signal) is sometimes obtained from a chest strap with one or more metallic sensors that is worn by the living subject during use. Alternatively, or in addition to, the second sensor time-domain signal 201 (e.g., the second sensor time-domain signal) is sometimes obtained from a thumb apparatus or a hand apparatus with one or more metallic sensing elements (e.g., electrodes) that are touched (e.g., with the living subject's thumbs) and/or held onto (e.g., with the living subject's hands) by the living subject during use. After optionally being pre-processed by analog front end 120/122 to produce filtered sensor time-domain signal 207—time-domain signals 201 are conditioned by a signal conditioning module 130/132.

In some embodiments, the conditioning of a respective sensor time-domain signal includes (608) upsampling the respective sensor time-domain signal to produce an intermediate signal and low pass filtering the intermediate signal to produce a respective time-domain signal. For example, as shown in FIG. 2B, filtered sensor time-domain signal 207—after conversion from an analog signal to a corresponding digital signal—is upsampled (e.g., by upsampler 212, FIG. 2B) to produce a first intermediate signal (e.g., first intermediate signal 214, FIG. 2B). For example, as explained above, if the original sampling rate of the digital representation of the analog filtered sensor time-domain signal corresponds to 500 Hz, the first intermediate signal (e.g., first intermediate signal 214) produced by upsampler 212 has a sampling rate used in conventional audio applications (e.g., 48 kHz). First intermediate signal 214 is then low pass filtered (e.g., by digital low pass filter(s) 216, FIG. 2B) to produce the time-domain signal or a signal corresponding to the time-domain signal (e.g., time-domain signal 218, FIG. 2B).

The digital processor system produces (610) representations of a plurality of acoustic signals. Each representation of an acoustic signal of the plurality of acoustic signals corresponds to a respective time-domain signal of the two or more time-domain signals. For each respective representation of an acoustic signal, the respective representation is produced by concurrently generating (612) a plurality of acoustic parameters, including a plurality of time-varying acoustic parameters.

In this context, parameters are "concurrently generated" even if they are literally generated serially by single-threaded processor, when the resulting parameters are used or applied concurrently for generating an audio signal, or a representation of an audio signal. Typically, two or more concurrently generated parameters are generated or updated in response to a stream of digital signal values corresponding to the respective time-domain signal.

One or more of the plurality of time-varying acoustic parameters is modulated in accordance with at least the signal value of the respective time-domain signal. For example, as explained above with reference to FIG. 2C, signal modulator(s) 140/142 (optionally included in digital processor 160) concurrently generate(s) a set of acoustic parameters, including a plurality of time-varying acoustic parameters. In some embodiments, as described in relation to FIG. 2C above, the plurality of acoustic parameters includes a vibrato or frequency-control parameter (e.g., frequency-control parameter 222-a), a vowel-control parameter (e.g., vowel-control parameter 222-b), and/or a time-varying amplitude or intensity-control parameter (e.g., intensity-control parameter 222-c). In some embodiments, the set of acoustic parameters includes a pitch-control parameter (e.g., pitch-control parameter 222-d) and/or a sonic identity parameter (e.g., sonic identity parameter 222-e).

Attention is now directed towards operations 614-646, through which the digital processing system generates the plurality of acoustic parameters, and controls properties and/or features of acoustic parameters, in accordance with various embodiments.

In some embodiments, for a respective acoustic signal of the plurality of acoustic signals, generating the plurality of acoustic parameters includes (614) generating a frequency-control parameter in accordance with the signal value of the time-domain signal. For example, as described above with reference to FIG. 2C, signal modulator(s) 140/142 (optionally included in a digital processor system) includes vibrato modulator 220-a, which generates frequency-control parameter 222-a.

In some embodiments, for a respective acoustic signal of the plurality of acoustic signals, generating the plurality of acoustic parameters includes (615) generating a frequency-control parameter by: obtaining (616) a base frequency corresponding to the respective acoustic signal; modulating (618) the base frequency in accordance with the signal value of the time-domain signal to produce a signal-dependent variation of the base frequency; and generating (620) the frequency-control parameter corresponding to the signal-dependent variation of the base frequency. For example, as explained above, vibrato modulator (e.g., Vibrato Modulator 220-a, FIG. 2C) generates a control parameter (e.g., a frequency control parameter) for controlling the amount of vibrato (which can be considered to be the amount of frequency variation) produced by a music or audio synthesizer. In some implementations (e.g., implementations in which pitch and vibrato are controlled during audio synthesis by separate parameters) the frequency-control parameter is independent of the base frequency or pitch, while in other implementations the frequency-control parameter incorporates the base frequency or pitch.

In some embodiments, for a respective acoustic signal of the plurality of acoustic signals, generating (622) the plurality of acoustic parameters includes generating a vowel-control parameter by selecting (624) a sequence of acoustic waveform patterns from a set of N acoustic waveform patterns. The set of N acoustic waveform patterns is arranged in a predefined order, where N is an integer greater than 2. In some embodiments, the sequence of acoustic waveform patterns includes (626) a sequence of vowel waveform patterns. The vowel-control parameter is further generated by modulating (628) a rate of selecting the sequence of acoustic waveform patterns in accordance with the signal value of the time-domain signal, to produce a signal-dependent rate of variation of acoustic waveform patterns. The vowel-control parameter is then generated (630) corresponding to the signal-dependent rate of variation of acoustic waveform patterns.

For example, as described above, vowel modulator (e.g., vowel-control parameter 222-b) modulates a rate of sequentially selecting acoustic waveform patterns from a set of 12 acoustic waveform patterns in accordance with the signal value of the time-domain signal (e.g., time-domain signal 218, FIG. 2C). For example, for an increase in signal value of the time-domain signal (e.g., time-domain signal 218), vowel modulator (e.g., vowel-control parameter 222-b) selects (e.g., scans through) a sequence of acoustic waveform patterns from a set of 12 acoustic waveform patterns more rapidly or at an increased rate; conversely, for a decrease in signal value of the time-domain signal (e.g., time-domain signal 218), vowel modulator (e.g., vowel-control parameter 222-b) selects (e.g., scans through) a sequence of acoustic waveform patterns from a set of 12 acoustic waveform patterns more gradually (e.g., slowly) or at a decreased rate.

In some embodiments, for a respective acoustic signal of the plurality of acoustic signals, generating the plurality of acoustic parameters includes (632): computing (634) a time-varying amplitude value in accordance with the signal value of the time-domain signal, and generating (636) a time-varying control parameter corresponding to the computed time-varying amplitude value.

For example, as described above in relation to FIG. 2C, an intensity modulator (e.g., intensity modulator 220-c, FIG. 2C) computes a time-varying amplitude value in accordance with the signal value of the time-domain signal (e.g., time-domain signal 218, FIG. 2C) and generates a time-varying intensity-control parameter (e.g., intensity-control parameter 222-c, FIG. 2C) corresponding to the computed time-varying amplitude value. In some implementations, for an increase in signal value of the time-domain signal (e.g., time-domain signal 218), the time-varying amplitude value—and corresponding time-varying intensity-control parameter (e.g., intensity-control parameter 222-c)—computed by intensity modulator (e.g., intensity modulator 220-c) increases. Conversely, for a decrease in signal value of the time-domain signal (e.g., time-domain signal 218), the time-varying amplitude value—and corresponding time-varying intensity-control parameter (e.g., Intensity-Control Parameter 222-c)—computed by intensity modulator (e.g., intensity modulator 220-c) decreases.

In some embodiments, for a respective acoustic signal of the plurality of acoustic signals, generating the plurality of acoustic parameters includes (632) selecting (638) a base frequency. The base frequency for each respective acoustic signal is (640) audibly distinct from the base frequency of any other acoustic signal of the plurality of acoustic signals. Generating the plurality of acoustic parameters further includes generating (642) a time-varying pitch-control parameter in accordance with the selected base frequency and the signal value of the time-domain signal. For example, as shown in FIG. 2C, signal modulator(s) 140/142 (optionally included in digital processor 160) include pitch modulator 220-d, which generates pitch-control parameter 222-d in accordance a signal value of the time-domain signal (e.g., time-domain signal 218), and optionally in accordance with a selected base frequency (e.g., corresponding to a spatial location of sensing the time-domain signal).

In some embodiments, for a respective acoustic signal of the plurality of acoustic signals, generating the plurality of acoustic parameters includes (632) selecting (644) a sonic identity in accordance with a spatial location, with respect to the subject's body, of a sensor for sensing the time-domain signal. Generating the plurality of acoustic parameters further includes generating (646) an identity-control parameter in accordance with the selected sonic identity.

For example, as shown in FIG. 1, sensor(s) 110/112 are located at different spatial locations on the living subject's body (e.g., different spatial location in the brain, or on the skull, corresponding to EEG signals, or differential spatial location on the chest, arms, legs, or abdomen corresponding to ECG signals) for sensing the time-domain signal (e.g., sensor time-domain signal 201), and a sonic identity is selected in accordance with a spatial location on the body of the living subject. In this example, for a time-domain signal obtained from the left hemisphere in the brain, a sonic identity is selected corresponding to the sonic identity of (e.g., acoustic characteristics defining or associated with) a violin (or a first "voice"); for a time-domain signal obtained from the right hemisphere in the brain, a sonic identity is selected corresponding to the sonic identity of (e.g., acoustic characteristics defining or associated with) a guitar (or as second "voice"); and for a time-domain signal obtained from the heart, a sonic identity is selected corresponding to the sonic identity of (e.g., acoustic characteristics defining or associated with) a clarinet. In some implementations, the sonic identity is simply the base frequency of each generated acoustic signal (or representation of an acoustic signal), while in some other implementations, the sonic identity determines both the base frequency and one or more parameters (e.g., multipliers, offsets, etc.) that are used while generating the acoustic parameters corresponding to each time-domain signal (e.g., corresponding to each sensor signal being sonified). In some embodiments, a distinct sonic identity is selected in accordance with each lead of a multi-lead electrocardiogram (e.g., distinct from the sonic identity selected in accordance with any other lead of the multi-lead electrocardiogram or any other time-signal obtained).

Returning now to operation 610, each representation of an acoustic signal of the plurality of acoustic signals is further produced by combining (648) the concurrently generated plurality of acoustic parameters to produce the respective representation of the acoustic signal corresponding to the respective time-domain signal. For example, as shown in FIG. 2C, synthesizer module 150/152 (optionally included in digital processor 160) combines the concurrently generated set of acoustic parameters generated by signal modulator(s) 140/142 to produce a representation of an acoustic signal (representation of acoustic signal 230) corresponding to the time-domain signal (e.g., time-domain signal 218).

In some embodiments, combining the concurrently generated plurality of acoustic parameters includes (650) applying the concurrently generated plurality of acoustic parameters to a music synthesizer or music synthesizer module to produce the representation of an acoustic signal. In some embodiments, the music synthesizer or music synthesizer module uses (652) frequency modulation synthesis. For example, as shown in FIG. 2C, synthesizer module 150/152 uses frequency modulation synthesis implemented on frequency modulation synthesizer 224.

In some embodiments, the at least one time-domain signal representing brain activity includes (654) a plurality of time-domain signals representing brain activity at a plurality of distinct locations of a brain of the subject. Producing representations of a plurality of acoustic signals includes producing representations of three or more acoustic signals, each corresponding to the heart activity or one of the plurality of distinct locations of the brain of the subject. As described above, in some embodiments, the three or more acoustic signals are (or comprise) (656) audibly distinct acoustic signals. In some embodiments, the three or more acoustic signals include (658) audibly distinct sonic identities. For example, in some embodiments, the one or more time-domain signals representing brain activity include two or more time-domain signals representing brain activity including a first time-domain signal representing left lobe brain activity and a second time-domain signal representing right lobe brain activity.

In some embodiments, the digital processing system combines (660) the representations of each of the plurality of acoustic signals to produce a combined acoustic signal (e.g., using combiner module 170, FIG. 2D). In some embodiments, the combined acoustic signal, in audible form, manifests (662) one or more audibly discernible variations across a plurality of stages of an abnormal electrical event in the subject's body. For example, in some embodiments, the abnormal electrical event is (664) one of: an epileptic seizure, an ST-elevated myocardial infarction, a supraventricular tachycardia (SVT) event, an atrial fibrillation event, a ventral fibrillation event, a stroke, and/or an episode of fasciculation (i.e., muscle twitching).

In some other embodiments, audio signals corresponding to the aforementioned two or more representations of acoustic signals, are combined to produce a combined audio signal. For example, the combined acoustic signal, corresponding to representations of the plurality of acoustic signals, is generated (e.g., generated "in the air") by concurrent production of two or more individual acoustic signals within a physical space or in a manner that enables the concurrently produced acoustic signals to be heard concurrently by a human listener. Alternatively, audio signals corresponding to the aforementioned two or more representations of acoustic signals, are recorded on separate tracks, or directed to distinct speakers, for concurrent production as acoustic signals. In some embodiments, a plurality of acoustic signals, each corresponding to one of more of the aforementioned representations of acoustic signals, are recorded on distinct tracks, where the distinct tracks are configured to enable concurrent playback of the acoustic signals recorded in those tracks.

In some embodiments, the abnormal electrical event is a supraventricular tachycardia (SVT) event and the audible form of the combined acoustic signal is provided to the living subject (e.g., as sound output by headphones or a speaker system) as a feedback mechanism for the subject while the subject undergoes vagal maneuvers to quell the SVT event. In some embodiments, the event is a stroke and the acoustic form of the combined acoustic signals is provided to field medical personnel (e.g., paramedics, emergency medical technicians, and the like) as a manner through which a working differential diagnosis can be ascertained to differentiate between, for example, an ischemic stroke, a hemorrhagic stroke, a diabetic emergency, etc.

Alternatively, in some embodiments, the living subject under the effects of anesthesia. The combined acoustic signal, in audible form, is provided to a doctor (e.g., an anesthesiologist) so that the doctor can determine a depth of the effects of the anesthesia. If the patient is not sufficiently anesthetized, the nervous system's response to an incision can generate an immediate response in the combined signal which may be more evident to the doctor than, for example, a displayed signal on a computer monitor.

Alternatively, or in addition to, in some embodiments, the combined acoustic signal, in audible form, manifests one or more audibly discernible variations of the subject's response to an external stimulus (e.g., visual and/or aural stimuli). For example, in some embodiments, the external stimulus is a video game, physical game, and/or exercise, and the combined acoustic signal is provided to the subject as a custom soundtrack.

While method 600 has been described with reference to at least one time-domain signal representing brain activity and at least one time-domain signal representing heart activity, one of ordinary skill in the art will recognize that either or both of the at least one time-domain signal representing brain activity and/or at least one time-domain signal representing heart activity may be replaced by a time-domain signal representing another bodily function. For example, in various embodiments, the at least one time-domain signal representing brain activity and/or at least one time-domain signal representing heart activity may be replaced by one of: a pulse oximetry signal, a capnography signal, a photoplethysmography signal, an electroencephalography (EEG) signal, and/or an electromyography (EMG) signal. Alternatively, one or ordinary skill in the art will recognize that method 600 may modified to make use of at least one time-domain signal representing brain activity, at least one time-domain signal representing heart activity, and at least one time-domain signal representing neither heart activity nor brain activity.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method of sonifying electrical signals obtained from a living subject, the method comprising:
obtaining, with one or more processors, two or more time-domain signals, including at least one time-domain signal representing brain activity and at least one time-domain signal representing heart activity, each of the one or more time-domain signals having a time-varying signal value;
producing representations of a plurality of acoustic signals with the one or more processors, wherein each representation of an acoustic signal of the plurality of acoustic signals corresponds to a respective time-domain signal of the two or more time-domain signals and is produced by:
concurrently generating a plurality of acoustic parameters, including a plurality of time-varying acoustic parameters, wherein one or more of the plurality of time-varying acoustic parameters is modulated in accordance with at least the signal value of the respective time-domain signal; and
combining the concurrently generated plurality of acoustic parameters to produce the representation of the acoustic signal corresponding to the respective time-domain signal;
combining the representations of each of the plurality of acoustic signals with the one or more processors to produce a musical combined acoustic signal; and
audibly providing, with one or more speakers, the musical combined acoustic signal to the living subject for feedback therapy for the living subject or to a living person other than the living subject for determining brain activity of the living subject, the musical combined acoustic signal comprising one or more audibly discernible variations representative of brain activity, and the feedback therapy or the determining of brain activity being based on the one or more audibly discernible variations.

2. The method of claim 1, wherein the one or more speakers comprise one or more of a headphone or speaker system.

3. The method of claim 1, further comprising performing said method, independently, on first and second living subjects, producing, with the one or more processors, first and second combined acoustic signals corresponding to the first and second living subjects, respectively, and audibly providing, with the one or more speakers, the first combined acoustic signal to the second living subject and audibly providing, with the one or more speakers, the second combined acoustic signal to the first living subject.

4. The method of claim 1, wherein the combined acoustic signal, in audible form, manifests the one or more audibly discernible variations across a plurality of stages of an abnormal electrical event in the subject's body.

5. The method of claim 4, wherein the abnormal electrical event is one of: an epileptic seizure, an ST-elevated myocardial infarction, a supraventricular tachycardia (SVT) event, an atrial fibrillation event, a ventral fibrillation event, a stroke, and/or an episode of fasciculation.

6. The method of claim 1, wherein the at least one time-domain signal representing brain activity is obtained by conditioning a sensor time-domain signal with the one or more processors, the sensor time-domain signal being obtained from a sensor embedded in a particular location of a brain.

7. The method of claim 1, wherein:
the at least one time-domain signal representing brain activity is obtained by conditioning a first sensor time-domain signal obtained from a first dry-contact sensor; and
the at least one time-domain signal representing heart activity is obtained by conditioning a second sensor time-domain signal obtained from a second dry-contact sensor.

8. The method of claim 7, wherein the conditioning of a respective sensor time-domain signal comprises upsampling the respective sensor time-domain signal with the one or more processors to produce an intermediate signal and low pass filtering the intermediate signal with the one or more processors to produce a respective time-domain signal.

9. The method of claim 1 wherein:
the at least one time-domain signal representing brain activity includes a plurality of time-domain signals representing brain activity at a plurality of distinct locations of a brain of the subject; and
producing representations of a plurality of acoustic signals further comprises producing representations of three or more acoustic signals, each corresponding to the heart activity or one of the plurality of distinct locations of the brain of the subject.

10. The method of claim 9, wherein the three or more acoustic signals comprise audibly distinct acoustic signals.

11. The method of claim 1, wherein, for a respective acoustic signal of the plurality of acoustic signals, generating the plurality of acoustic parameters includes:
selecting a base frequency; and
generating a time-varying pitch-control parameter in accordance with the selected base frequency and the signal value of the time-domain signal.

12. The method of claim 11, wherein the base frequency for each respective acoustic signal is audibly distinct from the base frequency of any other acoustic signal of the plurality of acoustic signals.

13. The method of claim 1, wherein, for a respective acoustic signal of the plurality of acoustic signals, generating the plurality of acoustic parameters includes:
selecting a sonic identity in accordance with a spatial location, with respect to the subject's body, of a sensor for sensing the time-domain signal; and
generating an identity-control parameter in accordance with the selected sonic identity.

14. A system for sonifying brain signals, comprising:
one or more sensors configured to be affixed to a body of a living subject;
one or more processors;
memory;
one or more programs, wherein the one or more programs are stored in the memory and configured to be executed by the one or more processors, the one or more programs including instructions for:
(i) obtaining two or more time-domain signals, including at least one time-domain signal representing brain activity and at least one time-domain signal representing heart activity, each of the one or more time-domain signals having a time-varying signal value, at least one of the two or more time-domain signals being obtained from the one or more sensors;
(ii) producing representations of a plurality of acoustic signals, wherein each representation of an acoustic signal of the plurality of acoustic signals corresponds to a respective time-domain signal of the two or more time-domain signals and is produced by:

(a) concurrently generating a plurality of acoustic parameters, including a plurality of time-varying acoustic parameters, wherein one or more of the plurality of time-varying acoustic parameters is modulated in accordance with at least the signal value of the respective time-domain signal; and (b) combining the concurrently generated plurality of acoustic parameters to produce the representation of the acoustic signal corresponding to the respective time-domain signal; and (iii) combining the representations of each of the plurality of acoustic signals to produce a musical combined acoustic signal; and one or more speakers for audibly providing the musical combined acoustic signal to the living subject for feedback therapy for the living subject or to a living person other than the living subject for determining brain activity of the living subject, the musical combined acoustic signal comprising one or more audibly discernible variations representative of brain activity, and the feedback therapy or the determining of brain activity being based on the one or more audibly discernible variations.

15. The system of claim 14, wherein the one or more speakers comprises one or more of a headphone or speaker system.

16. The system of claim 15, wherein the abnormal electrical event is one of: an epileptic seizure, an ST-elevated myocardial infarction, a supraventricular tachycardia (SVT) event, an atrial fibrillation event, a ventral fibrillation event, a stroke, and/or an episode of fasciculation.

17. The system of claim 14, wherein the at least one time-domain signal representing brain activity is obtained by conditioning a sensor time-domain signal obtained from a sensor embedded in a particular location of a brain.

18. The system of claim 14, wherein:
the at least one time-domain signal representing brain activity is obtained by conditioning a first sensor time-domain signal obtained from a first dry-contact sensor; and
the at least one time-domain signal representing heart activity is obtained by conditioning a second sensor time-domain signal obtained from a second dry-contact sensor.

19. The system of claim 18, wherein the conditioning of a respective sensor time-domain signal comprises upsampling the respective sensor time-domain signal to produce an intermediate signal and low pass filtering the intermediate signal to produce a respective time-domain signal.

20. The system of claim 14, wherein:
the at least one time-domain signal representing brain activity includes a plurality of time-domain signals representing brain activity at a plurality of distinct locations of a brain of the subject; and
producing representations of a plurality of acoustic signals further comprises producing representations of three or more acoustic signals, each corresponding to the heart activity or one of the plurality of distinct locations of the brain of the subject.

21. The system of claim 20, wherein the three or more acoustic signals comprise audibly distinct acoustic signals.

22. The system of claim 14, wherein, for a respective acoustic signal of the plurality of acoustic signals, generating the plurality of acoustic parameters includes:
selecting a base frequency; and
generating a time-varying pitch-control parameter in accordance with the selected base frequency and the signal value of the time-domain signal.

23. The system of claim 22, wherein the base frequency for each respective acoustic signal is audibly distinct from the base frequency of any other acoustic signal of the plurality of acoustic signals.

24. The system of claim 14, wherein, for a respective acoustic signal of the plurality of acoustic signals, generating the plurality of acoustic parameters includes:
selecting a sonic identity in accordance with a spatial location, with respect to the subject's body, of a sensor for sensing the time-domain signal; and
generating an identity-control parameter in accordance with the selected sonic identity.

* * * * *